US011427824B2

(12) United States Patent
Buj Bello et al.

(10) Patent No.: US 11,427,824 B2
(45) Date of Patent: *Aug. 30, 2022

(54) COMPOSITIONS AND METHODS FOR THE TREATMENT OF MYOTONIC DYSTROPHY

(71) Applicants: GENETHON, Evry (FR); INSERM (INSTITUT NATIONAL DE LA SANTE ET DE LA RECHERCHE MEDICALE), Paris (FR)

(72) Inventors: Ana Maria Buj Bello, Paris (FR); Mirella Lo Scrudato, Paris (FR)

(73) Assignees: GENETHON, Evry (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 480 days.

This patent is subject to a terminal disclaimer.

(21) Appl. No.: 16/345,743

(22) PCT Filed: Oct. 27, 2017

(86) PCT No.: PCT/EP2017/077674
§ 371 (c)(1),
(2) Date: Apr. 29, 2019

(87) PCT Pub. No.: WO2018/078134
PCT Pub. Date: May 3, 2018

(65) Prior Publication Data
US 2020/0140867 A1     May 7, 2020

(30) Foreign Application Priority Data

Oct. 28, 2016 (EP) .................................... 16306427

(51) Int. Cl.
C12N 15/113 (2010.01)
A61P 21/00 (2006.01)
C12N 9/22 (2006.01)
C12N 15/10 (2006.01)
C12N 15/90 (2006.01)

(52) U.S. Cl.
CPC .......... *C12N 15/1137* (2013.01); *A61P 21/00* (2018.01); *C12N 9/22* (2013.01); *C12N 15/102* (2013.01); *C12N 15/907* (2013.01); *C12N 2310/20* (2017.05); *C12N 2740/15041* (2013.01); *C12N 2750/14141* (2013.01)

(58) Field of Classification Search
CPC .... C12N 15/1137; C12N 9/22; C12N 15/102; C12N 15/907; C12N 2310/20; C12N 2740/15041; C12N 2750/14141; A61P 21/00

See application file for complete search history.

(56) References Cited

U.S. PATENT DOCUMENTS

2018/0100144 A1    4/2018 Buj Bello et al.

FOREIGN PATENT DOCUMENTS

| WO | WO 2015/089351 | 6/2015 | |
|----|----|----|----|
| WO | WO 2015/173436 | 11/2015 | |
| WO | WO 2016/174056 | 11/2016 | |
| WO | WO-2016179112 A1 * | 11/2016 | ........... C12N 15/111 |
| WO | WO 2018/078131 | 5/2018 | |

OTHER PUBLICATIONS

Friedland et al (Genome Biology (2015) 16:257, 10 pages) (Year: 2015).*
Ran et al (Nature 520, Extended Data Fig. 3 (2015)) (Year: 2015).*
Ran, F. A. et al. "In vivo genome editing using *Staphylococcus aureus* Cas9" *Nature*, Apr. 9, 2015, pp. 1-28, vol. 520, No. 7546.
Van Agtmaal, E. L. et al. "CRISPR/Cas9-Induced (CTG•CAG)$_n$ Repeat Instability in the Myotonic Dystrophy Type 1 Locus: Implications for Therapeutic Genome Editing" *Molecular Therapy*, Jan. 2017, pp. 24-43, vol. 25, No. 1.
Written Opinion in International Application No. PCT/EP2017/077674, dated Dec. 19, 2017, pp. 1-6.

* cited by examiner

*Primary Examiner* — Richard A Schnizer
(74) *Attorney, Agent, or Firm* — Saliwanchik, Lloyd & Eisenschenk

(57) ABSTRACT

The present invention relates to compositions and methods for the treatment of myotonic dystrophy.

Figure 4:
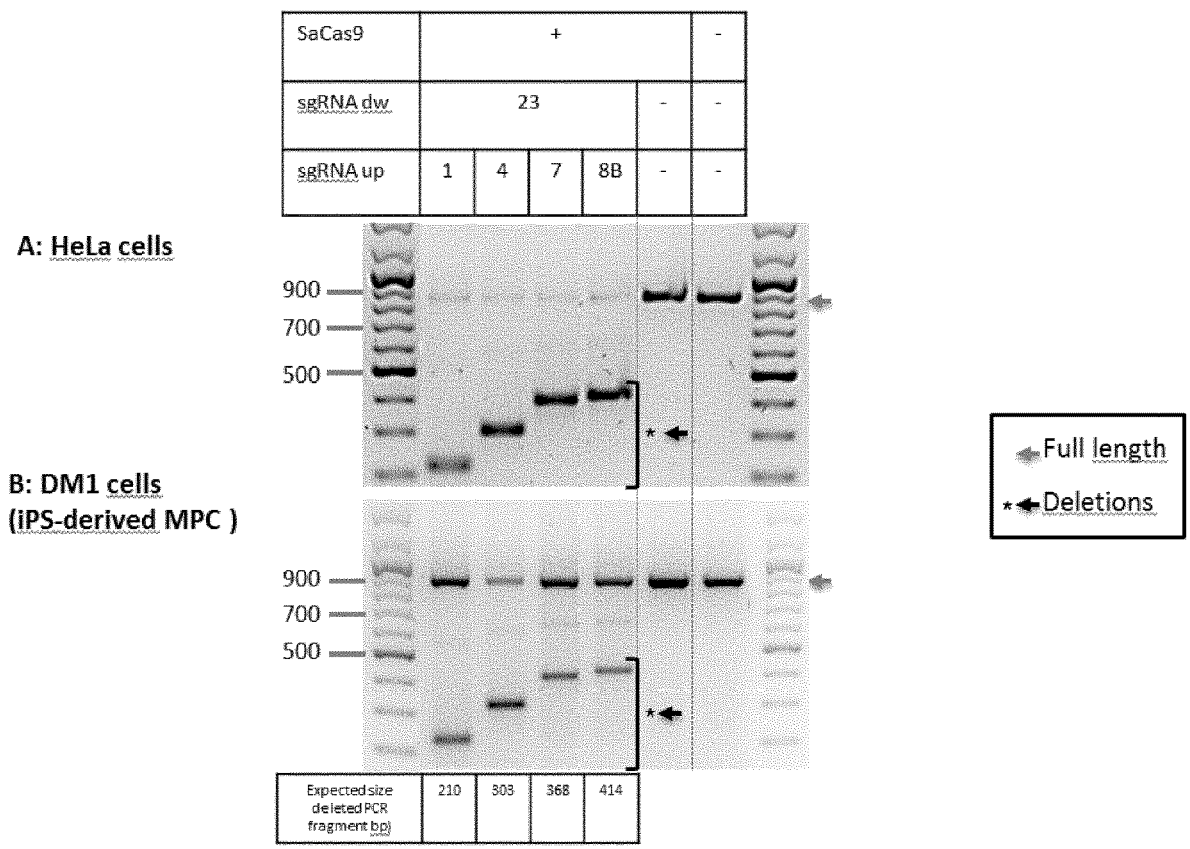

22 Claims, 9 Drawing Sheets
Specification includes a Sequence Listing.

Addgene 61591
(pX601-AAV6CMC::NLS-SaCas9-NLS-3xHA-bGHpA;U6::BsaI-sgRNA, Feng Zhang Lab)
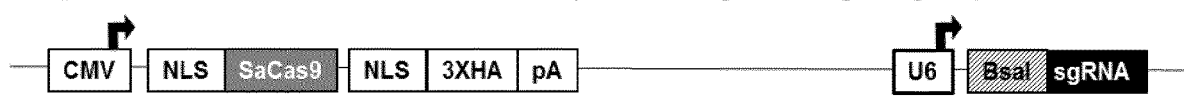
MLS43
(promoter change)
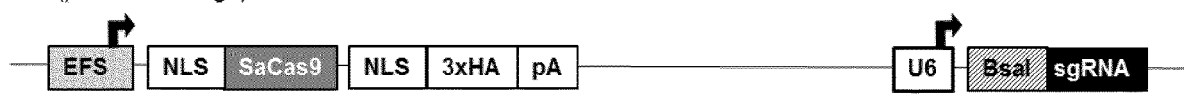
MLS47
(addition of a second sgRNA scaffold containing the sgRNA protospacer cloning site BbsI)
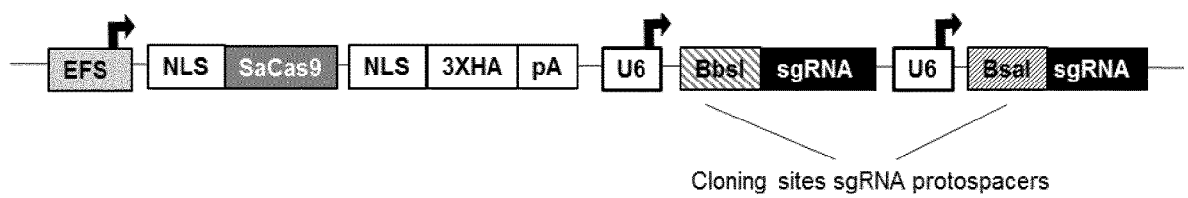
Cloning sites sgRNA protospacers
Figure 1

| number | protospacer sequence [5'->3']** | Length | Sa sgRNA protospacer * genomic target sequence (not underscored) and PAM (underscored) [5'->3'] | Genomic position # (start-end) | Strand | % cutting by TIDE |
|---|---|---|---|---|---|---|
| before CTG repeat | | | | | | |
| 1 | GCCCCGGAGTCGAAGACAGTTC (SEQ ID NO:19) | 22 | GCCCCGGAGTCGAAGACAGTTCTAGGGT (SEQ ID NO:30) | 45770460 45770487 | + | 47.4 |
| 4 | GCAGTTCACAACCGCTCCGAGC (SEQ ID NO:20) | G + 21 | GCAGTTCACAACCGCTCCGAGCGTGGGT (SEQ ID NO:31) | 45770377 45770403 | - | 42.4 |
| 7 | GCGGCCGGCGAACGGGGCTCG (SEQ ID NO:21) | 21 | GCGGCCGGCGAACGGGGCTCGAAGGGT (SEQ ID NO:32) | 45770282 45770308 | - | 43.8 |
| 8B | GGCTCGAAGGGTCCTTGTAGCC (SEQ ID NO:22) | 22 | GGCTCGAAGGGTCCTTGTAGCCGGGAAT (SEQ ID NO:33) | 45770266 45770293 | - | 42 |
| after CTG repeat | | | | | | |
| 10 | GCGGCCAGGCTGAGGCCCTGAC (SEQ ID NO:23) | G + 21 | CGGCCAGGCTGAGGCCCTGACGTGGAT (SEQ ID NO:34) | 45770151 45770177 | - | 7.8 |
| 15B | GGGGGGCGCGGGATCCCCGAAAAA (SEQ ID NO:24) | 24 | GGGGGGCGCGGGATCCCCGAAAAAGCGGGT (SEQ ID NO:35) | 45769946 45769975 | + | 3.3 |
| 17A | GGCTCCGCCCCGCTTCGGCGGT (SEQ ID NO:25) | 21 | GGCTCCGCCCCGCTTCGGCGGTTTGGAT (SEQ ID NO:36) | 45769887 45769913 | - | 1.8 |
| 17B | GCCGGCTCCGCCCCGCTTCGGCGGT (SEQ ID NO:26) | 24 | GCCGGCTCCGCCCCGCTTCGGCGGTTTGGAT (SEQ ID NO:37) | 45769887 45769916 | - | 2 |
| 19 | GAAAACGTGGATTGGGGTTGTT (SEQ ID NO:27) | G+21 | AAAACGTGGATTGGGGTTGTTGGGGGT (SEQ ID NO:38) | 45769819 45769845 | + | 1.1 |
| 22 | GGGGTCTCAGTGCATCCAAAAC (SEQ ID NO:28) | 22 | GGGGTCTCAGTGCATCCAAAACGTGGAT (SEQ ID NO:39) | 45769802 45769829 | + | 7.9 |
| 23 | GACAATAAATACCGAGGAATGT (SEQ ID NO:29) | 22 | GACAATAAATACCGAGGAATGTCGGGGT (SEQ ID NO:40) | 45769779 45769806 | + | 48.3 |

* sgRNA scaffold comes from plasmid pX601-AAV-CMV::NLS-SaCas9-NLS-3xHA-bGHpA;U6::BsaI-sgRNA (Addgene number 61591)
** = 5' specific part of the sgRNA; transcribed sequence has the same sequence except that the base U replaces T
G = not part of the target sequence, it has been added to optimize the transcription of the sgRNA from U6 promoter
reference genome: Human GRCh38/hg38 (ucsc/Blat)

Figure 2

```
  1           CTTGACAGAAGCTGAGGCCCCG 5' (sgRNA 1, 22nt)
  1 TGAACCCTAGAACTGTCTTCGACTCCGGGGCCCCGTTGGAAGACTGAGTGCCCGGGGCAC

G\
 61                             CAGTTCACAACCGCTCCGAGC 3' (sgRNA 4, 21nt+G)
 61 GGCACAGAAGCCGCGCCCACCGCCTGCCAGTTCACAACCGCTCCGAGCGTGGGTCTCCGC

121 CCAGCTCCAGTCCTGTGATCCGGGCCCGCCCCCTAGCGGCCGGGGAGGGAGGGGCCGGGT

181                   GGCTCGAAGGGTCCTTGTAGCC 3' (sgRNA 8B, 22nt)
181    GCGGCCGGCGAACGGGGCTCG 3' (sgRNA 7, 21nt)
181 CCGCGGCCGGCGAACGGGGCTCGAAGGGTCCTTGTAGCCGGGAATGCTGCTGCTGCTGCT

241 GCTGCTGCTGCTGCTGCTGCTGCTGCTGCTGCTGCTGCTGGGGGGATCACAGAC

G\
301            CGGCCAGGCTGAGGCCCTGAC 3' (sgRNA 10,21nt+G)
301 CATTTCTTTCTTTCGGCCAGGCTGAGGCCCTGACGTGGATGGGCAAACTGCAGGCCTGGG

361 AAGGCAGCAAGCCGGGCCGTCCGTGTTCCATCCTCCACGCACCCCACCTATCGTTGGTT

421 CGCAAAGTGCAAAGCTTTCTTGTGCATGACGCCCTGCTCTGGGGAGCGTCTGGCGCGATC

481                                          AAAAAGCCCCTAGGGCGCG
481 TCTGCCTGCTTACTCGGGAAATTTGCTTTTGCCAAACCCGCTTTTTCGGGGATCCCGCGC

541 GGGGG 5' (sgRNA 15B, 24nt)
541                             GGCTCCGCCCGCTTCGGCGGT 3' (sgRNA 17A, 21nt)
541                          GCCGGCTCCGCCCGCTTCGGCGGT 3' (sgRNA 17B, 24nt)
541 CCCCCTCCTCACTTGCGCTGCTCTCGGAGCCCCAGCCGGCTCCGCCCGCTTCGGCGGTTT

601                                                      TTGTTGGGG
601 GGATATTTATTGACCTCGTCCTCCGACTCGCTGACAGGCTACAGGACCCCCAACAACCCC

G 5' (sgRNA 19, 21+G)
661 TTAGGTGCAAAA/
661                         TGTAAGGAGCCATAAATAACAG 5' (sgRNA 23, 22nt)
661        CAAAACCTACGTGACTCTGGGG 5' (sgRNA 22, 22nt)
661 AATCCACGTTTTGGATGCACTGAGACCCCGACATTCCTCGGTATTTATTGTCTGTCCCCA

721 CCTAGGACCCCCACCCCCGACCCTCGCGAATAAAA
```

Sequences of the sgRNAs are represented as un-transcribed sequences containing the nucleotide T instead U

*TGA*: stop codon DMPK gene

NNNNNN: PAM sequence

G\: nucleotide G that is part of the sgRNA sequence but that does not anneal the DNA

CTGCTG...CTGCTGCT: CTG repeat

*TAAAA*: polyA signal

Figure 3

CTGn deletion by Sa sgRNAs:

▶ 1 and 23

SEQ ID NO: 93
WT  CTGGCGCCGCCCAGGAGCGCCCAGGAGCGCCCGCCGCCGCGCCCGCCGCTCCTGA<u>ACCCCTG</u>A<u>GAACTGTCTTCGACTCCGGGGC</u>···(CTG)n···<u>ACCCCG</u>ACATTCCTCGGTATTTATTGTCTGTCCCACCTAGGACCCCGACCCTCG    SEQ ID NO: 94
Δ1-23  CTGGCGCCGCCCAGGAGCGCCCAGGAGCGCCCGCCGCCGCGCCCGCCGCTCCTAGAA------------------------------------------TTCCTCGGTATTTATTGTCTGTCCCACCTAGGACCCCGACCCTCG    SEQ ID NO: 96

SEQ ID NO: 95

▶ 4 and 23

SEQ ID NO: 97
WT  CGGGGCACGGCACGAGAAGCGCCGCCGCCGCCTGCCAGTTCACAACCGCTCCGAGC<u>GTGGGT</u>···(CTG)n···<u>ACCCCG</u>ACATTCCTCGGTATTTATTGTCTGTCCCACCTAGGACCCCGACCCTCG    SEQ ID NO: 98
Δ4-23  CGGGGCACGGCACGAGAAGCGCCGCCGCCGCCTGCCAGTTCACAACCGCTCCG---------------------------------------------TTCCTCGGTATTTATTGTCTGTCCCACCTAGGACCCCGACCCTCG    SEQ ID NO: 100

SEQ ID NO: 99

▶ 7 and 23

SEQ ID NO: 101
WT  GCCCCCTAGCGGCCGGGAGGAGGAGGCGCCGGGTCCGGCCGGCCGGCGGGCGGAACGGGGCTCG<u>AAGGGT</u>···(CTG)n···<u>ACCCCG</u>ACATTCCTCGGTATTTATTGTCTGTCCCACCTAGGACCCCGACCCTCG    SEQ ID NO: 102
Δ7-23  GCCCCCTAGCGGCCGGGAGGAGGAGGCGCCGGGTCCGGCCGGCCGGCGGGCGGAACGGGGC--------------------------------------TTCCTCGGTATTTATTGTCTGTCCCACCTAGGACCCCGACCCTCG    SEQ ID NO: 104

SEQ ID NO: 103

▶ 8B and 23

SEQ ID NO: 105
WT  GGAGGGAGGGGCGGGTCCGCGGCCGGGTCCGAAGGGTCCTTGTAGCC<u>GGGAAT</u>···(CTG)n···<u>ACCCCG</u>ACATTCCTCGGTATTTATTGTCTGTCCCACCTAGGACCCCGACCCTCG    SEQ ID NO: 106
Δ8B-23  GGAGGGAGGGGCGGGTCCGCGGCCGGGTCCGAAGGGTCCTTGTA-----------------------------------------TTCCTCGGTATTTATTGTCTGTCCCACCTAGGACCCCGACCCTCG    SEQ ID NO: 108

SEQ ID NO: 107

Figure 5

A
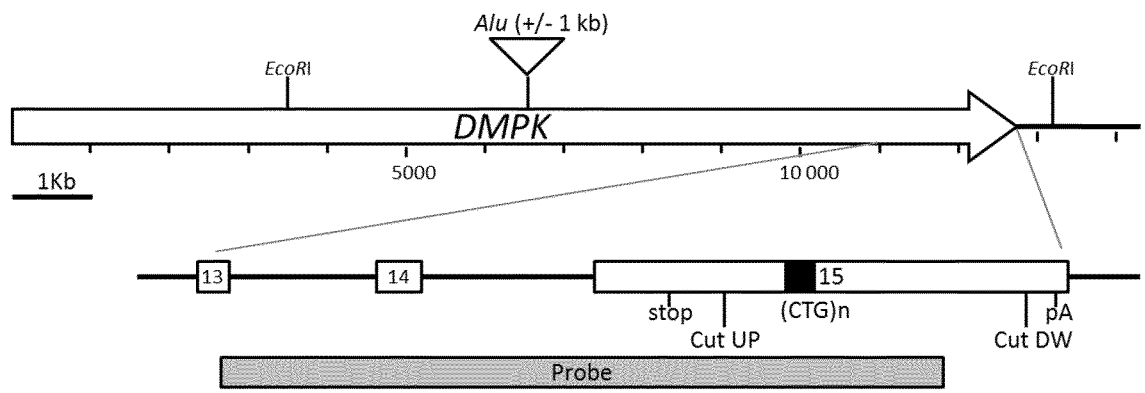
B
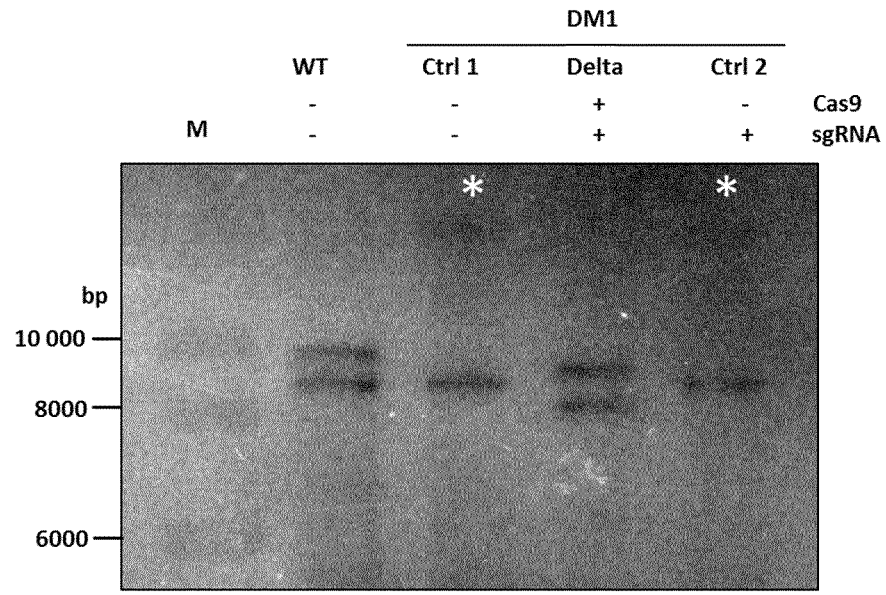
C
| Myoblasts | Allele | (CTG)n | Alu | EcoRI band (bp) |
|---|---|---|---|---|
| WT | 1 | 5 | + | 9637 |
| | 2 | 14 | - | 8664 |
| DM1→DM1 Delta | 1 | 2600 → 0 | + | 17422 → 9094 |
| | 2 | 13 → 0 | - | 8661 → 8094 |
Figure 7

```
                            SEQUENCE LISTING

<160> NUMBER OF SEQ ID NOS: 108

<210> SEQ ID NO 1
<211> LENGTH: 22
<212> TYPE: RNA
<213> ORGANISM: artificial
<220> FEATURE:
<223> OTHER INFORMATION: Guide sequence sgRNA 1

<400> SEQUENCE: 1
gccccggagu cgaagacagu uc                                              22

<210> SEQ ID NO 2
<211> LENGTH: 21
<212> TYPE: RNA
<213> ORGANISM: artificial
<220> FEATURE:
<223> OTHER INFORMATION: Guide sequence sgRNA 4

<400> SEQUENCE: 2
caguucacaa ccgcuccgag c                                               21

<210> SEQ ID NO 3
<211> LENGTH: 21
<212> TYPE: RNA
<213> ORGANISM: artificial
<220> FEATURE:
<223> OTHER INFORMATION: Guide sequence sgRNA 7

<400> SEQUENCE: 3
gcggccggcg aacggggcuc g                                               21

<210> SEQ ID NO 4
<211> LENGTH: 22
<212> TYPE: RNA
<213> ORGANISM: artificial
<220> FEATURE:
<223> OTHER INFORMATION: Guide sequence sgRNA 8B

<400> SEQUENCE: 4
ggcucgaagg guccuuguag cc                                              22

<210> SEQ ID NO 5
<211> LENGTH: 22
<212> TYPE: RNA
<213> ORGANISM: artificial
<220> FEATURE:
<223> OTHER INFORMATION: Guide sequence sgRNA 23

<400> SEQUENCE: 5
gacaauaaau accgaggaau gu                                              22

<210> SEQ ID NO 6
<211> LENGTH: 81
<212> TYPE: RNA
<213> ORGANISM: artificial
<220> FEATURE:
<223> OTHER INFORMATION: Sa sgRNA constant moiety

<400> SEQUENCE: 6
guuuuaguac ucuggaaaca gaaucuacua aaacaaggca aaaugccgug uuuaucucgu     60
```

```
caacuuguug gcgagauuuu u                                             81

<210> SEQ ID NO 7
<211> LENGTH: 15
<212> TYPE: RNA
<213> ORGANISM: artificial
<220> FEATURE:
<223> OTHER INFORMATION: minimum guide sequence sgRNA 1

<400> SEQUENCE: 7
agucgaagac aguuc                                                    15

<210> SEQ ID NO 8
<211> LENGTH: 15
<212> TYPE: RNA
<213> ORGANISM: artificial
<220> FEATURE:
<223> OTHER INFORMATION: minimum guide sequence sgRNA 4

<400> SEQUENCE: 8
acaaccgcuc cgagc                                                    15

<210> SEQ ID NO 9
<211> LENGTH: 15
<212> TYPE: RNA
<213> ORGANISM: artificial
<220> FEATURE:
<223> OTHER INFORMATION: minimum guide sequence sgRNA 7

<400> SEQUENCE: 9
ggcgaacggg gcucg                                                    15

<210> SEQ ID NO 10
<211> LENGTH: 15
<212> TYPE: RNA
<213> ORGANISM: artificial
<220> FEATURE:
<223> OTHER INFORMATION: minimum guide sequence sgRNA 8B

<400> SEQUENCE: 10
agggaccuug uagcc                                                    15

<210> SEQ ID NO 11
<211> LENGTH: 15
<212> TYPE: RNA
<213> ORGANISM: artificial
<220> FEATURE:
<223> OTHER INFORMATION: minimun guide sequence sgRNA 23

<400> SEQUENCE: 11
aauaccgagg aaugu                                                    15

<210> SEQ ID NO 12
<211> LENGTH: 103
<212> TYPE: DNA
<213> ORGANISM: artificial
<220> FEATURE:
<223> OTHER INFORMATION: coding sequence Sa sgRNA 1

<400> SEQUENCE: 12
gccccggagt cgaagacagt tcgttttagt actctggaaa cagaatctac taaaacaagg   60
caaaatgccg tgtttatctc gtcaacttgt tggcgagatt ttt                    103

<210> SEQ ID NO 13
<211> LENGTH: 103
```

```
<212> TYPE: DNA
<213> ORGANISM: artificial
<220> FEATURE:
<223> OTHER INFORMATION: coding sequence Sa sgRNA 4

<400> SEQUENCE: 13
gcagttcaca accgctccga gcgttttagt actctggaaa cagaatctac taaaacaagg     60
caaaatgccg tgtttatctc gtcaacttgt tggcgagatt ttt                      103

<210> SEQ ID NO 14
<211> LENGTH: 102
<212> TYPE: DNA
<213> ORGANISM: artificial
<220> FEATURE:
<223> OTHER INFORMATION: coding sequence Sa sgRNA 7

<400> SEQUENCE: 14
gcggccggcg aacggggctc ggttttagta ctctggaaac agaatctact aaaacaaggc     60
aaaatgccgt gtttatctcg tcaacttgtt ggcgagattt tt                       102

<210> SEQ ID NO 15
<211> LENGTH: 103
<212> TYPE: DNA
<213> ORGANISM: artificial
<220> FEATURE:
<223> OTHER INFORMATION: coding sequence Sa sgRNA 8B

<400> SEQUENCE: 15
ggctcgaagg gtccttgtag ccgttttagt actctggaaa cagaatctac taaaacaagg     60
caaaatgccg tgtttatctc gtcaacttgt tggcgagatt ttt                      103

<210> SEQ ID NO 16
<211> LENGTH: 103
<212> TYPE: DNA
<213> ORGANISM: artificial
<220> FEATURE:
<223> OTHER INFORMATION: coding sequence Sa sgRNA 23

<400> SEQUENCE: 16
gacaataaat accgaggaat gtgttttagt actctggaaa cagaatctac taaaacaagg     60
caaaatgccg tgtttatctc gtcaacttgt tggcgagatt ttt                      103

<210> SEQ ID NO 17
<211> LENGTH: 249
<212> TYPE: DNA
<213> ORGANISM: artificial
<220> FEATURE:
<223> OTHER INFORMATION: U6 promoter

<400> SEQUENCE: 17
gagggcctat ttcccatgat tccttcatat ttgcatatac gatacaaggc tgttagagag     60
ataattggaa ttaatttgac tgtaaacaca agatattag tacaaaatac gtgacgtaga    120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacacc                                                            249

<210> SEQ ID NO 18
<211> LENGTH: 22
<212> TYPE: RNA
<213> ORGANISM: artificial
<220> FEATURE:
```

<223> OTHER INFORMATION: Guide sequence sgRNA 4 + G

<400> SEQUENCE: 18
gcaguucaca accgcuccga gc                                              22

<210> SEQ ID NO 19
<211> LENGTH: 22
<212> TYPE: DNA
<213> ORGANISM: artificial
<220> FEATURE:
<223> OTHER INFORMATION: Protospacer seq 1

<400> SEQUENCE: 19
gccccggagt cgaagacagt tc                                              22

<210> SEQ ID NO 20
<211> LENGTH: 22
<212> TYPE: DNA
<213> ORGANISM: artificial
<220> FEATURE:
<223> OTHER INFORMATION: Protospacer seq 4

<400> SEQUENCE: 20
gcagttcaca accgctccga gc                                              22

<210> SEQ ID NO 21
<211> LENGTH: 21
<212> TYPE: DNA
<213> ORGANISM: artificial
<220> FEATURE:
<223> OTHER INFORMATION: Protospacer seq 7

<400> SEQUENCE: 21
gcggccggcg aacggggctc g                                               21

<210> SEQ ID NO 22
<211> LENGTH: 22
<212> TYPE: DNA
<213> ORGANISM: artificial
<220> FEATURE:
<223> OTHER INFORMATION: Protospacer seq 8B

<400> SEQUENCE: 22
ggctcgaagg gtccttgtag cc                                              22

<210> SEQ ID NO 23
<211> LENGTH: 22
<212> TYPE: DNA
<213> ORGANISM: artificial
<220> FEATURE:
<223> OTHER INFORMATION: Protospacer seq 10

<400> SEQUENCE: 23
gcggccaggc tgaggccctg ac                                              22

<210> SEQ ID NO 24
<211> LENGTH: 24
<212> TYPE: DNA
<213> ORGANISM: artificial
<220> FEATURE:
<223> OTHER INFORMATION: Protospacer seq 15B

<400> SEQUENCE: 24 gggggggcgcg ggatccccga aaaa                                           24

```
<210> SEQ ID NO 25
<211> LENGTH: 21
<212> TYPE: DNA
<213> ORGANISM: artificial
<220> FEATURE:
<223> OTHER INFORMATION: Protospacer seq 17A

<400> SEQUENCE: 25
ggctccgccc gcttcggcgg t                                              21

<210> SEQ ID NO 26
<211> LENGTH: 24
<212> TYPE: DNA
<213> ORGANISM: artificial
<220> FEATURE:
<223> OTHER INFORMATION: Protospacer seq 17B

<400> SEQUENCE: 26
gccggctccg cccgcttcgg cggt                                           24

<210> SEQ ID NO 27
<211> LENGTH: 22
<212> TYPE: DNA
<213> ORGANISM: artificial
<220> FEATURE:
<223> OTHER INFORMATION: Protospacer seq 19

<400> SEQUENCE: 27
gaaaacgtgg attggggttg tt                                             22

<210> SEQ ID NO 28
<211> LENGTH: 22
<212> TYPE: DNA
<213> ORGANISM: artificial
<220> FEATURE:
<223> OTHER INFORMATION: Protospacer seq 22

<400> SEQUENCE: 28
ggggtctcag tgcatccaaa ac                                             22

<210> SEQ ID NO 29
<211> LENGTH: 22
<212> TYPE: DNA
<213> ORGANISM: artificial
<220> FEATURE:
<223> OTHER INFORMATION: Protospacer seq 23

<400> SEQUENCE: 29
gacaataaat accgaggaat gt                                             22

<210> SEQ ID NO 30
<211> LENGTH: 28
<212> TYPE: DNA
<213> ORGANISM: artificial
<220> FEATURE:
<223> OTHER INFORMATION: Genomic target sequence + PAM 1

<400> SEQUENCE: 30
gccccggagt cgaagacagt tctagggt                                       28

<210> SEQ ID NO 31
<211> LENGTH: 27
<212> TYPE: DNA
<213> ORGANISM: artificial
<220> FEATURE:
<223> OTHER INFORMATION: Genomic target sequence + PAM 4
```

```
<400> SEQUENCE: 31
cagttcacaa ccgctccgag cgtgggt                                          27

<210> SEQ ID NO 32
<211> LENGTH: 27
<212> TYPE: DNA
<213> ORGANISM: artificial
<220> FEATURE:
<223> OTHER INFORMATION: Genomic target sequence + PAM 7

<400> SEQUENCE: 32
gcggccggcg aacggggctc gaagggt                                          27

<210> SEQ ID NO 33
<211> LENGTH: 28
<212> TYPE: DNA
<213> ORGANISM: artificial
<220> FEATURE:
<223> OTHER INFORMATION: Genomic target sequence + PAM 8B

<400> SEQUENCE: 33
ggctcgaagg gtccttgtag ccgggaat                                         28

<210> SEQ ID NO 34
<211> LENGTH: 27
<212> TYPE: DNA
<213> ORGANISM: artificial
<220> FEATURE:
<223> OTHER INFORMATION: Genomic target sequence + PAM 10

<400> SEQUENCE: 34
cggccaggct gaggccctga cgtggat                                          27

<210> SEQ ID NO 35
<211> LENGTH: 30
<212> TYPE: DNA
<213> ORGANISM: artificial
<220> FEATURE:
<223> OTHER INFORMATION: Genomic target sequence + PAM 15B

<400> SEQUENCE: 35 gggggcgcg ggatccccga aaaagcgggt                                        30

<210> SEQ ID NO 36
<211> LENGTH: 27
<212> TYPE: DNA
<213> ORGANISM: artificial
<220> FEATURE:
<223> OTHER INFORMATION: Genomic target sequence + PAM 17A

<400> SEQUENCE: 36
ggctccgccc gcttcggcgg tttggat                                          27

<210> SEQ ID NO 37
<211> LENGTH: 30
<212> TYPE: DNA
<213> ORGANISM: artificial
<220> FEATURE:
<223> OTHER INFORMATION: Genomic target sequence + PAM 17B

<400> SEQUENCE: 37
gccggctccg cccgcttcgg cggtttggat                                       30

<210> SEQ ID NO 38
<211> LENGTH: 27
```

```
<212> TYPE: DNA
<213> ORGANISM: artificial
<220> FEATURE:
<223> OTHER INFORMATION: Genomic target sequence + PAM 19

<400> SEQUENCE: 38
aaaacgtgga ttggggttgt tgggggt                                             27

<210> SEQ ID NO 39
<211> LENGTH: 28
<212> TYPE: DNA
<213> ORGANISM: artificial
<220> FEATURE:
<223> OTHER INFORMATION: Genomic target sequence + PAM 22

<400> SEQUENCE: 39
ggggtctcag tgcatccaaa acgtggat                                            28

<210> SEQ ID NO 40
<211> LENGTH: 28
<212> TYPE: DNA
<213> ORGANISM: artificial
<220> FEATURE:
<223> OTHER INFORMATION: Genomic target sequence + PAM 23

<400> SEQUENCE: 40
gacaataaat accgaggaat gtcggggt                                            28

<210> SEQ ID NO 41
<211> LENGTH: 755
<212> TYPE: DNA
<213> ORGANISM: artificial
<220> FEATURE:
<223> OTHER INFORMATION: DMPK 3'-UTR from the stop codon to the polyA

<400> SEQUENCE: 41
tgaaccctag aactgtcttc gactccgggg ccccgttgga agactgagtg cccggggcac         60
ggcacagaag ccgcgcccac cgcctgccag ttcacaaccg ctccgagcgt gggtctccgc        120
ccagctccag tcctgtgatc cgggcccgcc ccctagcggc cggggaggga ggggccgggt        180
ccgcggccgg cgaacggggc tcgaagggtc cttgtagccg ggaatgctgc tgctgctgct        240
gctgctgctg ctgctgctgc tgctgctgct gctgctgctg ctgctggggg gatcacagac        300
catttctttc tttcggccag gctgaggccc tgacgtggat gggcaaactg caggcctggg        360
aaggcagcaa gccgggccgt ccgtgttcca tcctccacgc accccaccct atcgttggtt        420
cgcaaagtgc aaagctttct tgtgcatgac gccctgctct ggggagcgtc tggcgcgatc        480
tctgcctgct tactcgggaa atttgctttt gccaaacccg cttttttcggg gatcccgcgc        540 ccccctcctc acttgcgctg ctctcggagc cccagccggc tccgcccgct tcggcggttt        600
ggatatttat tgacctcgtc ctccgactcg ctgacaggct acaggacccc caacaacccc        660
aatccacgtt ttggatgcac tgagaccccg acattcctcg gtatttattg tctgtcccca        720
cctaggaccc ccaccccga ccctcgcgaa taaaa                                    755

<210> SEQ ID NO 42
<211> LENGTH: 1114
<212> TYPE: PRT
<213> ORGANISM: artificial
<220> FEATURE:
<223> OTHER INFORMATION: SaCas9 from plasmid Addgene61591

<400> SEQUENCE: 42
```

```
Met Ala Pro Lys Lys Lys Arg Lys Val Gly Ile His Gly Val Pro Ala
1               5                   10                  15
Ala Lys Arg Asn Tyr Ile Leu Gly Leu Asp Ile Gly Ile Thr Ser Val
            20                  25                  30
Gly Tyr Gly Ile Ile Asp Tyr Glu Thr Arg Asp Val Ile Asp Ala Gly
        35                  40                  45
Val Arg Leu Phe Lys Glu Ala Asn Val Glu Asn Asn Glu Gly Arg Arg
50                  55                  60
Ser Lys Arg Gly Ala Arg Leu Lys Arg Arg Arg His Arg Ile
65                  70                  75                  80
Gln Arg Val Lys Lys Leu Leu Phe Asp Tyr Asn Leu Leu Thr Asp His
                85                  90                  95
Ser Glu Leu Ser Gly Ile Asn Pro Tyr Glu Ala Arg Val Lys Gly Leu
            100                 105                 110
Ser Gln Lys Leu Ser Glu Glu Phe Ser Ala Ala Leu Leu His Leu
            115                 120                 125
Ala Lys Arg Arg Gly Val His Asn Val Asn Glu Val Glu Glu Asp Thr
    130                 135                 140
Gly Asn Glu Leu Ser Thr Lys Glu Gln Ile Ser Arg Asn Ser Lys Ala
145                 150                 155                 160
Leu Glu Glu Lys Tyr Val Ala Glu Leu Gln Leu Glu Arg Leu Lys Lys
                165                 170                 175
Asp Gly Glu Val Arg Gly Ser Ile Asn Arg Phe Lys Thr Ser Asp Tyr
            180                 185                 190
Val Lys Glu Ala Lys Gln Leu Leu Lys Val Gln Lys Ala Tyr His Gln
        195                 200                 205
Leu Asp Gln Ser Phe Ile Asp Thr Tyr Ile Asp Leu Leu Glu Thr Arg
    210                 215                 220
Arg Thr Tyr Tyr Glu Gly Pro Gly Glu Gly Ser Pro Phe Gly Trp Lys
225                 230                 235                 240
Asp Ile Lys Glu Trp Tyr Glu Met Leu Met Gly His Cys Thr Tyr Phe
                245                 250                 255
Pro Glu Glu Leu Arg Ser Val Lys Tyr Ala Tyr Asn Ala Asp Leu Tyr
            260                 265                 270
Asn Ala Leu Asn Asp Leu Asn Asn Leu Val Ile Thr Arg Asp Glu Asn
    275                 280                 285
Glu Lys Leu Glu Tyr Tyr Glu Lys Phe Gln Ile Ile Glu Asn Val Phe
                290                 295                 300
Lys Gln Lys Lys Lys Pro Thr Leu Lys Gln Ile Ala Lys Glu Ile Leu
305                 310                 315                 320
Val Asn Glu Glu Asp Ile Lys Gly Tyr Arg Val Thr Ser Thr Gly Lys
                325                 330                 335
Pro Glu Phe Thr Asn Leu Lys Val Tyr His Asp Ile Lys Asp Ile Thr
            340                 345                 350
Ala Arg Lys Glu Ile Ile Glu Asn Ala Glu Leu Leu Asp Gln Ile Ala
    355                 360                 365
Lys Ile Leu Thr Ile Tyr Gln Ser Ser Glu Asp Ile Gln Glu Glu Leu
370                 375                 380
Thr Asn Leu Asn Ser Glu Leu Thr Gln Glu Ile Glu Gln Ile Ser
385                 390                 395                 400
Asn Leu Lys Gly Tyr Thr Gly Thr His Asn Leu Ser Leu Lys Ala Ile
                405                 410                 415
Asn Leu Ile Leu Asp Glu Leu Trp His Thr Asn Asp Asn Gln Ile Ala
```

```
                420             425             430
Ile Phe Asn Arg Leu Lys Leu Val Pro Lys Val Asp Leu Ser Gln
            435             440             445
Gln Lys Glu Ile Pro Thr Thr Leu Val Asp Asp Phe Ile Leu Ser Pro
        450             455             460
Val Val Lys Arg Ser Phe Ile Gln Ser Ile Lys Val Ile Asn Ala Ile
465             470             475             480
Ile Lys Lys Tyr Gly Leu Pro Asn Asp Ile Ile Glu Leu Ala Arg
            485             490             495
Glu Lys Asn Ser Lys Asp Ala Gln Lys Met Ile Asn Glu Met Gln Lys
        500             505             510
Arg Asn Arg Gln Thr Asn Glu Arg Ile Glu Glu Ile Arg Thr Thr
    515             520             525
Gly Lys Glu Asn Ala Lys Tyr Leu Ile Glu Lys Ile Lys Leu His Asp
    530             535             540
Met Gln Glu Gly Lys Cys Leu Tyr Ser Leu Glu Ala Ile Pro Leu Glu
545             550             555             560
Asp Leu Leu Asn Asn Pro Phe Asn Tyr Glu Val Asp His Ile Ile Pro
            565             570             575
Arg Ser Val Ser Phe Asp Asn Ser Phe Asn Asn Lys Val Leu Val Lys
            580             585             590
Gln Glu Glu Asn Ser Lys Lys Gly Asn Arg Thr Pro Phe Gln Tyr Leu
        595             600             605
Ser Ser Ser Asp Ser Lys Ile Ser Tyr Glu Thr Phe Lys Lys His Ile
        610             615             620
Leu Asn Leu Ala Lys Gly Lys Gly Arg Ile Ser Lys Thr Lys Lys Glu
625             630             635             640
Tyr Leu Leu Glu Glu Arg Asp Ile Asn Arg Phe Ser Val Gln Lys Asp
            645             650             655
Phe Ile Asn Arg Asn Leu Val Asp Thr Arg Tyr Ala Thr Arg Gly Leu
            660             665             670
Met Asn Leu Leu Arg Ser Tyr Phe Arg Val Asn Asn Leu Asp Val Lys
        675             680             685
Val Lys Ser Ile Asn Gly Gly Phe Thr Ser Phe Leu Arg Arg Lys Trp
    690             695             700
Lys Phe Lys Lys Glu Arg Asn Lys Gly Tyr Lys His His Ala Glu Asp
705             710             715             720
Ala Leu Ile Ile Ala Asn Ala Asp Phe Ile Phe Lys Glu Trp Lys Lys
            725             730             735
Leu Asp Lys Ala Lys Lys Val Met Glu Asn Gln Met Phe Glu Glu Lys
        740             745             750
Gln Ala Glu Ser Met Pro Glu Ile Glu Thr Glu Gln Glu Tyr Lys Glu
        755             760             765
Ile Phe Ile Thr Pro His Gln Ile Lys His Ile Lys Asp Phe Lys Asp
    770             775             780
Tyr Lys Tyr Ser His Arg Val Asp Lys Lys Pro Asn Arg Glu Leu Ile
785             790             795             800
Asn Asp Thr Leu Tyr Ser Thr Arg Lys Asp Asp Lys Gly Asn Thr Leu
            805             810             815
Ile Val Asn Asn Leu Asn Gly Leu Tyr Asp Lys Asp Asn Asp Lys Leu
            820             825             830
Lys Lys Leu Ile Asn Lys Ser Pro Glu Lys Leu Leu Met Tyr His His
        835             840             845
```

-continued

Asp Pro Gln Thr Tyr Gln Lys Leu Lys Leu Ile Met Glu Gln Tyr Gly
            850                 855                 860

Asp Glu Lys Asn Pro Leu Tyr Lys Tyr Tyr Glu Glu Thr Gly Asn Tyr
865                 870                 875                 880

Leu Thr Lys Tyr Ser Lys Lys Asp Asn Gly Pro Val Ile Lys Lys Ile
                885                 890                 895

Lys Tyr Tyr Gly Asn Lys Leu Asn Ala His Leu Asp Ile Thr Asp Asp
            900                 905                 910

Tyr Pro Asn Ser Arg Asn Lys Val Val Lys Leu Ser Leu Lys Pro Tyr
                915                 920                 925

Arg Phe Asp Val Tyr Leu Asp Asn Gly Val Tyr Lys Phe Val Thr Val
            930                 935                 940

Lys Asn Leu Asp Val Ile Lys Lys Glu Asn Tyr Tyr Glu Val Asn Ser
945                 950                 955                 960

Lys Cys Tyr Glu Glu Ala Lys Lys Leu Lys Lys Ile Ser Asn Gln Ala
                965                 970                 975

Glu Phe Ile Ala Ser Phe Tyr Asn Asn Asp Leu Ile Lys Ile Asn Gly
            980                 985                 990

Glu Leu Tyr Arg Val Ile Gly Val Asn Asn Asp Leu Leu Asn Arg Ile
            995                 1000                1005

Glu Val Asn Met Ile Asp Ile Thr Tyr Arg Glu Tyr Leu Glu Asn
            1010                1015                1020

Met Asn Asp Lys Arg Pro Pro Arg Ile Ile Lys Thr Ile Ala Ser
            1025                1030                1035

Lys Thr Gln Ser Ile Lys Lys Tyr Ser Thr Asp Ile Leu Gly Asn
            1040                1045                1050

Leu Tyr Glu Val Lys Ser Lys Lys His Pro Gln Ile Ile Lys Lys
            1055                1060                1065

Gly Lys Arg Pro Ala Ala Thr Lys Lys Ala Gly Gln Ala Lys Lys
            1070                1075                1080

Lys Lys Gly Ser Tyr Pro Tyr Asp Val Pro Asp Tyr Ala Tyr Pro
            1085                1090                1095

Tyr Asp Val Pro Asp Tyr Ala Tyr Pro Tyr Asp Val Pro Asp Tyr
            1100                1105                1110

Ala

<210> SEQ ID NO 43
<211> LENGTH: 22
<212> TYPE: DNA
<213> ORGANISM: artificial
<220> FEATURE:
<223> OTHER INFORMATION: coding sequence guide sequence sgRNA 1

<400> SEQUENCE: 43
gccccggagt cgaagacagt tc                                          22

<210> SEQ ID NO 44
<211> LENGTH: 22
<212> TYPE: DNA
<213> ORGANISM: artificial
<220> FEATURE:
<223> OTHER INFORMATION: coding sequence guide sequence sgRNA 4

<400> SEQUENCE: 44
gcagttcaca accgctccga gc                                          22

```
<210> SEQ ID NO 45
<211> LENGTH: 21
<212> TYPE: DNA
<213> ORGANISM: artificial
<220> FEATURE:
<223> OTHER INFORMATION: coding sequence guide sequence sgRNA 7

<400> SEQUENCE: 45
gcggccggcg aacggggctc g                                              21

<210> SEQ ID NO 46
<211> LENGTH: 22
<212> TYPE: DNA
<213> ORGANISM: artificial
<220> FEATURE:
<223> OTHER INFORMATION: coding sequence guide sequence sgRNA 8B

<400> SEQUENCE: 46
ggctcgaagg gtccttgtag cc                                             22

<210> SEQ ID NO 47
<211> LENGTH: 22
<212> TYPE: DNA
<213> ORGANISM: artificial
<220> FEATURE:
<223> OTHER INFORMATION: coding sequence guide sequence sgRNA 23

<400> SEQUENCE: 47
gacaataaat accgaggaat gt                                             22

<210> SEQ ID NO 48
<211> LENGTH: 81
<212> TYPE: DNA
<213> ORGANISM: artificial
<220> FEATURE:
<223> OTHER INFORMATION: sgRNA constant moiety (as in the plasmid)

<400> SEQUENCE: 48
gttttagtac tctggaaaca gaatctacta aaacaaggca aaatgccgtg tttatctcgt    60
caacttgttg gcgagatttt t                                              81

<210> SEQ ID NO 49
<211> LENGTH: 40
<212> TYPE: DNA
<213> ORGANISM: artificial
<220> FEATURE:
<223> OTHER INFORMATION: primer

<400> SEQUENCE: 49
cgctcgagcg ccggcgtgag gctccggtgc ccgtcagtgg                          40

<210> SEQ ID NO 50
<211> LENGTH: 43
<212> TYPE: DNA
<213> ORGANISM: artificial
<220> FEATURE:
<223> OTHER INFORMATION: primer

<400> SEQUENCE: 50
cgcccgggtc gcgatcacga cacctgtgtt ctggcggcaa acc                      43

<210> SEQ ID NO 51
<211> LENGTH: 30
<212> TYPE: DNA
<213> ORGANISM: artificial
<220> FEATURE:
```

<223> OTHER INFORMATION: primer

<400> SEQUENCE: 51
gcgaccggtg ccaccatggc cccaaagaag                                    30

<210> SEQ ID NO 52
<211> LENGTH: 44
<212> TYPE: DNA
<213> ORGANISM: artificial
<220> FEATURE:
<223> OTHER INFORMATION: primer

<400> SEQUENCE: 52
cgcgtcgacc ttaagcgtaa tctggaacat cgtatgggta agcg                    44

<210> SEQ ID NO 53
<211> LENGTH: 32
<212> TYPE: DNA
<213> ORGANISM: artificial
<220> FEATURE:
<223> OTHER INFORMATION: primer

<400> SEQUENCE: 53
gcggtttaaa cgccaccatg gccccaaaga ag                                 32

<210> SEQ ID NO 54
<211> LENGTH: 39
<212> TYPE: DNA
<213> ORGANISM: artificial
<220> FEATURE:
<223> OTHER INFORMATION: primer

<400> SEQUENCE: 54
ccgcggccgc gcgagctcta ggaattctta agcgtaatc                          39

<210> SEQ ID NO 55
<211> LENGTH: 38
<212> TYPE: DNA
<213> ORGANISM: artificial
<220> FEATURE:
<223> OTHER INFORMATION: primer

<400> SEQUENCE: 55
ggaggtacct taagcaattg gacatagtcg tttaaacc                           38

<210> SEQ ID NO 56
<211> LENGTH: 31
<212> TYPE: DNA
<213> ORGANISM: artificial
<220> FEATURE:
<223> OTHER INFORMATION: primer

<400> SEQUENCE: 56
cctcacgtgt cctgcggccg caaaaatctc g                                  31

<210> SEQ ID NO 57
<211> LENGTH: 25
<212> TYPE: DNA
<213> ORGANISM: artificial
<220> FEATURE:
<223> OTHER INFORMATION: primer

<400> SEQUENCE: 57
caccgcggcc ggcgaacggg gctcg                                         25

<210> SEQ ID NO 58
<211> LENGTH: 25
<212> TYPE: DNA
<213> ORGANISM: artificial
<220> FEATURE:
<223> OTHER INFORMATION: primer

<400> SEQUENCE: 58
aaaccgagcc ccgttcgccg gccgc                                   25

<210> SEQ ID NO 59
<211> LENGTH: 26
<212> TYPE: DNA
<213> ORGANISM: artificial
<220> FEATURE:
<223> OTHER INFORMATION: primer

<400> SEQUENCE: 59
caccggctcg aagggtcctt gtagcc                                  26

<210> SEQ ID NO 60
<211> LENGTH: 26
<212> TYPE: DNA
<213> ORGANISM: artificial
<220> FEATURE:
<223> OTHER INFORMATION: primer

<400> SEQUENCE: 60
aaacggctac aaggaccctt cgagcc                                  26

<210> SEQ ID NO 61
<211> LENGTH: 26
<212> TYPE: DNA
<213> ORGANISM: artificial
<220> FEATURE:
<223> OTHER INFORMATION: primer

<400> SEQUENCE: 61
caccgcggcc aggctgaggc cctgac                                  26

<210> SEQ ID NO 62
<211> LENGTH: 26
<212> TYPE: DNA
<213> ORGANISM: artificial
<220> FEATURE:
<223> OTHER INFORMATION: primer

<400> SEQUENCE: 62
aaacgtcagg gcctcagcct ggccgc                                  26

<210> SEQ ID NO 63
<211> LENGTH: 28
<212> TYPE: DNA
<213> ORGANISM: artificial
<220> FEATURE:
<223> OTHER INFORMATION: primer

<400> SEQUENCE: 63
caccgggggg cgcgggatcc ccgaaaaa                                28

<210> SEQ ID NO 64
<211> LENGTH: 28
<212> TYPE: DNA
<213> ORGANISM: artificial
<220> FEATURE:
<223> OTHER INFORMATION: primer

<400> SEQUENCE: 64
aaactttttc ggggatcccg cgcccccc          28

<210> SEQ ID NO 65
<211> LENGTH: 25
<212> TYPE: DNA
<213> ORGANISM: artificial
<220> FEATURE:
<223> OTHER INFORMATION: primer

<400> SEQUENCE: 65
caccggctcc gcccgcttcg gcggt          25

<210> SEQ ID NO 66
<211> LENGTH: 25
<212> TYPE: DNA
<213> ORGANISM: artificial
<220> FEATURE:
<223> OTHER INFORMATION: primer

<400> SEQUENCE: 66
aaacaccgcc gaagcgggcg gagcc          25

<210> SEQ ID NO 67
<211> LENGTH: 28
<212> TYPE: DNA
<213> ORGANISM: artificial
<220> FEATURE:
<223> OTHER INFORMATION: primer

<400> SEQUENCE: 67
caccgccggc tccgcccgct cggcggt          28

<210> SEQ ID NO 68
<211> LENGTH: 28
<212> TYPE: DNA
<213> ORGANISM: artificial
<220> FEATURE:
<223> OTHER INFORMATION: primer

<400> SEQUENCE: 68
aaacaccgcc gaagcgggcg gagccggc          28

<210> SEQ ID NO 69
<211> LENGTH: 26
<212> TYPE: DNA
<213> ORGANISM: artificial
<220> FEATURE:
<223> OTHER INFORMATION: primer

<400> SEQUENCE: 69
caccgaaaac gtggattggg gttgtt          26

<210> SEQ ID NO 70
<211> LENGTH: 26
<212> TYPE: DNA
<213> ORGANISM: artificial
<220> FEATURE:
<223> OTHER INFORMATION: primer

<400> SEQUENCE: 70
aaacaacaac cccaatccac gttttc          26

<210> SEQ ID NO 71
<211> LENGTH: 26

```
<212> TYPE: DNA
<213> ORGANISM: artificial
<220> FEATURE:
<223> OTHER INFORMATION: primer

<400> SEQUENCE: 71
caccggggtc tcagtgcatc caaaac                                        26

<210> SEQ ID NO 72
<211> LENGTH: 26
<212> TYPE: DNA
<213> ORGANISM: artificial
<220> FEATURE:
<223> OTHER INFORMATION: primer

<400> SEQUENCE: 72
aaacgttttg gatgcactga gacccc                                        26

<210> SEQ ID NO 73
<211> LENGTH: 26
<212> TYPE: DNA
<213> ORGANISM: artificial
<220> FEATURE:
<223> OTHER INFORMATION: primer

<400> SEQUENCE: 73
caccgacaat aaataccgag gaatgt                                        26

<210> SEQ ID NO 74
<211> LENGTH: 26
<212> TYPE: DNA
<213> ORGANISM: artificial
<220> FEATURE:
<223> OTHER INFORMATION: primer

<400> SEQUENCE: 74
aaacacattc ctcggtattt attgtc                                        26

<210> SEQ ID NO 75
<211> LENGTH: 21
<212> TYPE: DNA
<213> ORGANISM: artificial
<220> FEATURE:
<223> OTHER INFORMATION: primer

<400> SEQUENCE: 75
gttcgccgtt gttctgtctc g                                             21

<210> SEQ ID NO 76
<211> LENGTH: 21
<212> TYPE: DNA
<213> ORGANISM: artificial
<220> FEATURE:
<223> OTHER INFORMATION: primer

<400> SEQUENCE: 76
tccagagctt tgggcagatg g                                             21

<210> SEQ ID NO 77
<211> LENGTH: 30
<212> TYPE: DNA
<213> ORGANISM: artificial
<220> FEATURE:
<223> OTHER INFORMATION: primer

<400> SEQUENCE: 77
```
ccgggtaccg ttcgccgttg ttctgtctcg                                              30

<210> SEQ ID NO 78
<211> LENGTH: 31
<212> TYPE: DNA
<213> ORGANISM: artificial
<220> FEATURE:
<223> OTHER INFORMATION: primer

<400> SEQUENCE: 78
ccgctctaga tccagagctt tgggcagatg g                                            31

<210> SEQ ID NO 79
<211> LENGTH: 21
<212> TYPE: DNA
<213> ORGANISM: artificial
<220> FEATURE:
<223> OTHER INFORMATION: primer

<400> SEQUENCE: 79
gtcccaggag ccaatcagag g                                                       21

<210> SEQ ID NO 80
<211> LENGTH: 21
<212> TYPE: DNA
<213> ORGANISM: artificial
<220> FEATURE:
<223> OTHER INFORMATION: primer

<400> SEQUENCE: 80
ctagctcctc ccagaccttc g                                                       21

<210> SEQ ID NO 81
<211> LENGTH: 23
<212> TYPE: DNA
<213> ORGANISM: artificial
<220> FEATURE:
<223> OTHER INFORMATION: primer

<400> SEQUENCE: 81
gcaagaccct gatgaagaag ctc                                                     23

<210> SEQ ID NO 82
<211> LENGTH: 19
<212> TYPE: DNA
<213> ORGANISM: artificial
<220> FEATURE:
<223> OTHER INFORMATION: primer

<400> SEQUENCE: 82
gacagaaggc cggatgctg                                                          19

<210> SEQ ID NO 83
<211> LENGTH: 20
<212> TYPE: DNA
<213> ORGANISM: artificial
<220> FEATURE:
<223> OTHER INFORMATION: primer

<400> SEQUENCE: 83
atcttcaagc tccgggccct                                                         20

<210> SEQ ID NO 84
<211> LENGTH: 20
<212> TYPE: DNA
<213> ORGANISM: artificial

```
<220> FEATURE:
<223> OTHER INFORMATION: primer

<400> SEQUENCE: 84
cagctctgcc tgaagatgtg                                          20

<210> SEQ ID NO 85
<211> LENGTH: 21
<212> TYPE: DNA
<213> ORGANISM: artificial
<220> FEATURE:
<223> OTHER INFORMATION: primer

<400> SEQUENCE: 85
gctgcccaat accaggtcaa c                                        21

<210> SEQ ID NO 86
<211> LENGTH: 22
<212> TYPE: DNA
<213> ORGANISM: artificial
<220> FEATURE:
<223> OTHER INFORMATION: primer

<400> SEQUENCE: 86
tggtgggaga aatgctgtat gc                                       22

<210> SEQ ID NO 87
<211> LENGTH: 20
<212> TYPE: DNA
<213> ORGANISM: artificial
<220> FEATURE:
<223> OTHER INFORMATION: primer

<400> SEQUENCE: 87
ttagaggagg tgatggagca                                          20

<210> SEQ ID NO 88
<211> LENGTH: 20
<212> TYPE: DNA
<213> ORGANISM: artificial
<220> FEATURE:
<223> OTHER INFORMATION: primer

<400> SEQUENCE: 88
gatactaagg actccatcgc                                          20

<210> SEQ ID NO 89
<211> LENGTH: 20
<212> TYPE: DNA
<213> ORGANISM: artificial
<220> FEATURE:
<223> OTHER INFORMATION: primer

<400> SEQUENCE: 89
ccaaagacag actctcagat                                          20

<210> SEQ ID NO 90
<211> LENGTH: 20
<212> TYPE: DNA
<213> ORGANISM: artificial
<220> FEATURE:
<223> OTHER INFORMATION: primer

<400> SEQUENCE: 90
aacatcgcca agggacctgc                                          20
```

<210> SEQ ID NO 91
<211> LENGTH: 21
<212> TYPE: DNA
<213> ORGANISM: artificial
<220> FEATURE:
<223> OTHER INFORMATION: primer

<400> SEQUENCE: 91
agaacctcaa tgatgtgctg g                                      21

<210> SEQ ID NO 92
<211> LENGTH: 21
<212> TYPE: DNA
<213> ORGANISM: artificial
<220> FEATURE:
<223> OTHER INFORMATION: primer

<400> SEQUENCE: 92
tcgtgttgac tctgatctcg g                                      21

<210> SEQ ID NO 93
<211> LENGTH: 62
<212> TYPE: DNA
<213> ORGANISM: Artificial Sequence
<220> FEATURE:
<223> OTHER INFORMATION: PCR product

<400> SEQUENCE: 93
ctggcgccgc ccaggagccg cccgcgctcc ctgaacccta gaactgtctt cgactccggg     60
gc                                                                   62

<210> SEQ ID NO 94
<211> LENGTH: 62
<212> TYPE: DNA
<213> ORGANISM: Artificial Sequence
<220> FEATURE:
<223> OTHER INFORMATION: PCR product

<400> SEQUENCE: 94
accccgacat tcctcggtat ttattgtctg tccccaccta ggaccccac ccccgaccct      60 cg                                                                   62

<210> SEQ ID NO 95
<211> LENGTH: 43
<212> TYPE: DNA
<213> ORGANISM: Artificial Sequence
<220> FEATURE:
<223> OTHER INFORMATION: PCR product

<400> SEQUENCE: 95
ctggcgccgc ccaggagccg cccgcgctcc ctgaacccta gaa                       43

<210> SEQ ID NO 96
<211> LENGTH: 53
<212> TYPE: DNA
<213> ORGANISM: Artificial Sequence
<220> FEATURE:
<223> OTHER INFORMATION: PCR product

<400> SEQUENCE: 96
ttcctcggta tttattgtct gtccccacct aggaccccca ccccgaccc tcg             53

<210> SEQ ID NO 97
<211> LENGTH: 62

```
<212> TYPE: DNA
<213> ORGANISM: Artificial Sequence
<220> FEATURE:
<223> OTHER INFORMATION: PCR product

<400> SEQUENCE: 97
cggggcacgg cacagaagcc gcgcccaccg cctgccagtt cacaaccgct ccgagcgtgg    60
gt                                                                  62

<210> SEQ ID NO 98
<211> LENGTH: 62
<212> TYPE: DNA
<213> ORGANISM: Artificial Sequence
<220> FEATURE:
<223> OTHER INFORMATION: PCR product

<400> SEQUENCE: 98
accccgacat tcctcggtat ttattgtctg tccccaccta ggaccccac ccccgaccct    60 cg                                                                  62

<210> SEQ ID NO 99
<211> LENGTH: 53
<212> TYPE: DNA
<213> ORGANISM: Artificial Sequence
<220> FEATURE:
<223> OTHER INFORMATION: PCR product

<400> SEQUENCE: 99
cggggcacgg cacagaagcc gcgcccaccg cctgccagtt cacaaccgct ccg           53

<210> SEQ ID NO 100
<211> LENGTH: 53
<212> TYPE: DNA
<213> ORGANISM: Artificial Sequence
<220> FEATURE:
<223> OTHER INFORMATION: PCR product

<400> SEQUENCE: 100
ttcctcggta tttattgtct gtccccacct aggacccca ccccgaccc tcg             53

<210> SEQ ID NO 101
<211> LENGTH: 62
<212> TYPE: DNA
<213> ORGANISM: Artificial Sequence
<220> FEATURE:
<223> OTHER INFORMATION: PCR product

<400> SEQUENCE: 101 gcccctagc ggccggggag ggaggggccg ggtccgcggc cggcgaacgg ggctcgaagg     60
gt                                                                  62

<210> SEQ ID NO 102
<211> LENGTH: 62
<212> TYPE: DNA
<213> ORGANISM: Artificial Sequence
<220> FEATURE:
<223> OTHER INFORMATION: PCR product

<400> SEQUENCE: 102
accccgacat tcctcggtat ttattgtctg tccccaccta ggaccccac ccccgaccct    60 cg                                                                  62

<210> SEQ ID NO 103
```

```
<211> LENGTH: 53
<212> TYPE: DNA
<213> ORGANISM: Artificial Sequence
<220> FEATURE:
<223> OTHER INFORMATION: PCR product

<400> SEQUENCE: 103 gcccctagc ggccggggag ggaggggccg ggtccgcggc cggcgaacgg ggc       53

<210> SEQ ID NO 104
<211> LENGTH: 53
<212> TYPE: DNA
<213> ORGANISM: Artificial Sequence
<220> FEATURE:
<223> OTHER INFORMATION: PCR product

<400> SEQUENCE: 104
ttcctcggta tttattgtct gtccccacct aggaccccca ccccgaccct cg       53

<210> SEQ ID NO 105
<211> LENGTH: 62
<212> TYPE: DNA
<213> ORGANISM: Artificial Sequence
<220> FEATURE:
<223> OTHER INFORMATION: PCR product

<400> SEQUENCE: 105
ggagggaggg gccgggtccg cggccggcga acggggctcg aagggtcctt gtagccggga       60
at                                                                     62

<210> SEQ ID NO 106
<211> LENGTH: 62
<212> TYPE: DNA
<213> ORGANISM: Artificial Sequence
<220> FEATURE:
<223> OTHER INFORMATION: PCR product

<400> SEQUENCE: 106
accccgacat tcctcggtat ttattgtctg tccccaccta ggaccccac ccccgaccct       60 cg                                                                     62

<210> SEQ ID NO 107
<211> LENGTH: 53
<212> TYPE: DNA
<213> ORGANISM: Artificial Sequence
<220> FEATURE:
<223> OTHER INFORMATION: PCR product

<400> SEQUENCE: 107
ggagggaggg gccgggtccg cggccggcga acggggctcg aagggtcctt gta       53

<210> SEQ ID NO 108
<211> LENGTH: 53
<212> TYPE: DNA
<213> ORGANISM: Artificial Sequence
<220> FEATURE:
<223> OTHER INFORMATION: PCR product

<400> SEQUENCE: 108
ttcctcggta tttattgtct gtccccacct aggaccccca ccccgaccct cg       53
```

COMPOSITIONS AND METHODS FOR THE TREATMENT OF MYOTONIC DYSTROPHY

CROSS-REFERENCE TO RELATED APPLICATION

This application is the U.S. national stage application of International Patent Application No. PCT/EP2017/077674, filed Oct. 27, 2017.

The Sequence Listing for this application is labeled "Seq-List-replace.txt" which was created on Feb. 1, 2022 and is 32 KB. The entire content of the sequence listing is incorporated herein by reference in its entirety.

FIELD OF THE INVENTION

The present invention relates to compositions and methods for the treatment of myotonic dystrophy.

BACKGROUND OF THE INVENTION

Nucleotide repeat expansions, especially trinucleotide repeat expansions, are involved in more than two dozen neurological and developmental disorders. One approach that has been proposed to treat these diseases is to shorten repeats to non-pathological lengths using highly specific nucleases (see for a review Richard G F, Trends Genet. 2015 April; 31(4):177-186).

Highly specific nucleases such as meganucleases, ZFNs, TALENs and CRISPR-Cas9 nucleases have been used in such strategies. However, the latter was considered by those skilled in the art to be inappropriate for the excision of trinucleotide repeat expansions (see Richard cited supra). Overall, TALENs were considered a more promising tool for shortening trinucleotide repeats.

Against this strong prejudice, the present inventors herein show that the CRISPR-Cas9 system may be implemented to excise nucleotide repeat expansions from genomic DNA in the DMPK gene, thereby providing a powerful and unexpected tool for treating myotonic dystrophy. More particularly, the present inventors discovered how to improve the excision efficiency of nucleotide repeat expansions within the DMPK gene, using Cas9 derived from *Staphylococcus aureus*.

SUMMARY OF THE INVENTION

The inventors have shown that, against the strong prejudice developed above, the CRISPR-Cas9 system may be efficient for the excision of nucleotide repeat expansions. The present invention relates to the improved tools for excising nucleotide repeat expansion within the DMPK gene, using CRISPR-Cas9 system derived from *S. aureus* with appropriate single guide RNAs (sgRNA).

In one aspect, disclosed herein are single guide RNA (sgRNA) molecules useful for specifically excising a nucleotide repeat expansion, especially a trinucleotide repeat expansion, from the 3'-UTR of the DMPK gene. The sgRNA molecules disclosed herein are able to bind by base-pairing a sequence complementary to a genomic DNA target (protospacer) sequence which is 5' or 3' from the targeted nucleotide expansion, and are able to recruit a Cas9 endonuclease to, or near, the site of hybridization between the sgRNA and genomic DNA. More precisely, the Cas9 endonuclease used herein for excising trinucleotide repeat expansion is derived from *Staphylococcus aureus* (SaCas9). The sgRNA molecules of the invention comprise all the sequence elements appropriate for inducing SaCas9-mediated double-strand breaks in the vicinity of the site of complementarity. In particular, the present application discloses sgRNA pairs appropriate for effecting an excision of the nucleotide repeat expansion present in the 3'-untranslated region (3'-UTR) of the DMPK gene, wherein the pair of sgRNAs comprises a first sgRNA which is complementary to a target genomic DNA sequence located 5' from the nucleotide repeat expansion and a second sgRNA which is complementary to a target genomic DNA sequence located 3' from the nucleotide repeat expansion. Said first sgRNA molecule is able to induce a double strand break within the 3'-UTR of the DMPK gene, 5' of the nucleotide repeat expansion in the presence of a Cas9 endonuclease. Said second sgRNA molecule is able to induce a double strand break within the 3'-UTR of the DMPK gene, 3' of the nucleotide repeat expansion in the presence of a Cas9 endonuclease. In the context of the invention, said Cas9 endonuclease is derived from *Staphylococcus aureus* (SaCas9), or said Cas9 endonuclease is a functional variant of a SaCas9.

The second sgRNA molecule comprises a guide sequence of 15-40 nucleotides comprising the nucleotide sequence shown in SEQ ID NO:11. In a particular embodiment, the guide sequence of the second sgRNA consists of a nucleotide sequence shown in SEQ ID NO:5.

In a particular embodiment, the first sgRNA molecule comprises a guide sequence of 15-40 nucleotides in length comprising the nucleotide sequence shown in SEQ ID NO:7, SEQ ID NO:8, SEQ ID NO:9 or SEQ ID NO:10.

Another aspect of the present invention relates to a sgRNA which comprises a sequence which is able to bind by base-pairing the sequence complementary to a target genomic DNA sequence which is located 5' or 3' from a nucleotide repeat expansion within the 3'-UTR of the DMPK gene;
  wherein the sgRNA molecule is able to induce a double strand break, within said 3'-UTR, either 5' or 3' of said nucleotide repeat expansion in the presence of a Cas9 endonuclease derived from *Staphylococcus aureus* (SaCas9), or of a Cas9 endonuclease that is a functional variant of a SaCas9;
  wherein said sgRNA comprises a guide sequence of 15-40 nucleotides comprising a sequence selected in the group consisting of SEQ ID NO:7-11.

Another aspect disclosed herein is the use of the CRISPR-Cas9 system for excising a nucleotide repeat expansion which is within the genomic DNA of a target cell, within the 3'UTR of the DMPK gene.

According to a further aspect, herein is disclosed a method for excising a nucleotide repeat expansion from the 3'-UTR of the DMPK gene in the genomic DNA of a cell, said method implementing the CRISPR-Cas9 system. The method may comprise introducing into the cell a pair of sgRNA molecules as described above and a gene coding a Cas9 endonuclease derived from *S. aureus* or a functional variant of a Cas9 endonuclease derived from *S. aureus*.

In another aspect, disclosed herein is a method for treating myotonic dystrophy type 1, wherein a nucleotide repeat expansion is excised from the DMPK gene using at least a pair of sgRNA molecules as described above and a Cas9 endonuclease derived from *S. aureus* or a functional variant of a Cas9 endonuclease derived from *S. aureus*.

In a particular embodiment, the nucleotide repeat expansion which is excised is a bi-, tri-, tetra-, penta or hexa-nucleotide repeat expansion located within the 3'-UTR of the DMPK gene, preferably a trinucleotide repeat expansion.

In a particular embodiment, the nucleotide repeat expansion may comprise 20 or more repeats, such as from 20 to 10000 repeats, in particular from 50 to 5000 repeats.

More specifically, the uses and methods of the invention may comprise introducing into a cell, such as a cell of a subject in need thereof:
(i) a first sgRNA molecule;
(ii) a second sgRNA molecule of 15-40 nucleotides in length comprising the sequence shown in SEQ ID NO:11; and
(iii) a CRISPR/Cas9 endonuclease derived from S. aureus, or a functional variant of CRISPR/Cas9 endonuclease derived from S. aureus;
wherein said first and second sgRNA are complementary to a sequence located 5' and 3' from a nucleotide repeat expansion within the 3'-UTR of the DMPK gene, respectively, thereby being appropriate for excising said nucleotide repeat expansion by inducing a double strand break within said 3'-UTR of the DMPK gene, 5' from the nucleotide repeat expansion, and a double strand break within said 3'-UTR of the DMPK gene, 3' from the nucleotide repeat expansion.

The invention provides a therapeutic strategy for the treatment of Myotonic Dystrophy type 1 (DM1).

The sgRNA molecules are designed to bind by base-pairing the complement to the genomic DNA target sequence in the 3'-UTR of the DMPK gene (otherwise referred to as the target sequence). This target sequence is called the protospacer and is located next to a nucleotide motif called PAM (Protospacer adjacent motif) that is specifically recognized by the implemented Cas9 endonuclease derived from S. aureus (SaCas9). In other words, the sgRNA molecule comprises guide RNA sequence corresponding to the protospacer sequence, in order to bind the complement to said proto spacer.

In some embodiments, the sgRNA molecule comprises a guide RNA sequence and a scaffold sequence, wherein the guide RNA sequence has from 15 to 40 nucleotides, in particular from 17 to 30 nucleotides, in particular from 20 to 25 nucleotides, such as 20, 21, 22, 23, 24 or 25 nucleotides. In particular embodiment, the sgRNA molecule has from 21 to 24 nucleotides. In a particular embodiment, the sgRNA molecule comprises a guide RNA sequence consisting of 21 or 24 nucleotides.

Another aspect relates to a vector encoding the sgRNA or a pair of sgRNA molecules as provided herein, the vector being preferably a plasmid or a viral vector, such as a rAAV vector or a lentiviral vector, in particular a rAAV vector.

In some embodiments, the SaCas9 endonuclease and/or the sgRNA molecules are expressed from one or several vectors, such as one or several plasmids or viral vectors. For example, the SaCas9 endonuclease may be expressed from a first vector, and the first and second sgRNA molecules may be either expressed from a single, second vector, or one from a second vector and the other one from a third vector. In another embodiment, all the elements necessary for the implementation of the CRISPR-Cas9 system are contained in a single vector. In another embodiment, SaCas9 endonuclease and sgRNA molecules are pre-assembled in vitro as a ribonucleoprotein complex (RNP) and then delivered to the cells by transfection methods. In a further embodiment, purified recombinant SaCas9 endonuclease protein and sgRNA molecules are synthetized in vitro and delivered separately to the cells.

In another embodiment, the pair of sgRNA molecules as described above is used in combination with another pair of sgRNA molecules. In this embodiment, the pairs of sgRNA molecules used in combination may be expressed from one or several vectors, such as one or several plasmids or viral vectors.

Another aspect relates to a target cell, which is transfected or transduced with the vector as herein described.

In a further aspect, it is herein disclosed a kit comprising a SaCas9 endonuclease, or a functional variant of a SaCas9 endonuclease, and a first and second sgRNA molecules as described above. In another aspect, it is herein disclosed a kit comprising a vector encoding a SaCas9 endonuclease and a vector encoding the first and/or the second sgRNA molecules as described above, or a single vector which expresses the SaCas9 endonuclease and one or both sgRNA molecules. As mentioned above, the vector(s) in the kit may be a plasmid vector or a viral vector. In a further aspect, it is herein disclosed a kit comprising ribonucleoprotein complex of SaCas9 endonuclease and sgRNA molecules. In another aspect, it is herein disclosed a kit comprising a recombinant SaCas9 endonuclease protein and sgRNA molecules separately synthetized in vitro. In addition, the kit according to the invention may include any further reagent (such as buffer(s) and/or one or more transfection reagent) or devices useful in the implementation of the methods and uses disclosed herein.

Other aspects and embodiments of the invention will be apparent in the following detailed description.

LEGENDS OF THE FIGURES

FIG. 1. SaCas9 and Sa sgRNA expression cassettes. Expression cassette for Cas9 from *Staphylococcus aureus* (SaCas9) from the addgene plasmid 61591 and its derivative plasmids MLS43 (containing the smaller promoter EFS instead the original CMV) and MLS47 (containing a second cassette for the expression of a second sgRNA). Sequence of Cas9 from *S. aureus* is the sequence with the following GenBank ID: CCK74173.1, Addgene plasmid 61591.

FIG. 2. Selected sgRNA protospacers, respective genomic targets and PAMs, and cutting efficiency. sgRNA protospacers, corresponding to the guide sequence of the sgRNAs, target a genomic region upstream or downstream the CTG repeat that goes from the stop codon of the gene DMPK to the polyA signal. The corresponding genomic target sequence and PAM (Protospacer adjacent motifs) specific to SaCas9 are presented. All sgRNAs were tested for their capability to cut the DNA at their genomic target. Results of cutting efficiency analyzed by the on line program TIDE are shown in the last column of the table.

FIG. 3. Genomic region surrounding the CTG repeats of the DMPK 3'-UTR from the stop codon of the gene (here arbitrarily indicated as nucleotide 1) to the polyA. Positions of all the sgRNAs tested within the DMPK 3'-UTR are indicated. Respective PAMs (Protospacer adjacent motifs), specific to SaCas9 are surrounded by a rectangle. CTG repeat, as well as DMPK stop codon and polyA (SEQ ID NO: 41) signal are underlined. sgRNA 1, 22nt (SEQ ID NO: 43); sgRNA 4, 21nt+G (SEQ ID NO: 44); sgRNA 7, 21nt (SEQ ID NO: 45); sgRNA 8B, 22nt (SEQ ID NO: 46); sgRNA 10, 21nt+G (SEQ ID NO: 23); sgRNA 15B, 24nt (SEQ ID NO: 24); sgRNA 17A, 21nt (SEQ ID NO: 25); sgRNA 17B, 24nt (SEQ ID NO: 26); sgRNA 19, 21+G (SEQ ID NO: 27); sgRNA 22, 22nt (SEQ ID NO: 28); and sgRNA 23, 22nt (SEQ ID NO: 47).

FIG. 4. Deletion of the DMPK CTG repeats in HeLa cells (A), and in DM1 human cells (iPS-derived MPC) (B). DMPK 3'-UTR region was PCR amplified from gDNA extracted from the indicated cell lines and PCR products have been separated in 1.5% agarose gel. Cells have been transfected with derivatives of plasmid MLS43 containing the indicated sgRNA couples. Downstream sgRNA 23 was tested with each of upstream sgRNAs 1, 4, 7 and 8B. gDNA from cells transfected only with a SaCas9 expressing plasmid or with a GFP expressing plasmid were used as control (ctrl). Expected size of the deleted PCR fragment is indicated in the panel below the agarose gel picture.

FIG. 5. Inspection by sequencing of the genomic region harboring the DMPK CTG repeats deletion. PCR products corresponding at those containing the CTG repeats deletion (indicated by the arrow in FIG. 4) have been extracted from the agarose gel, purified and sequenced by standard sequencing. The alignment between the undeleted genomic region (WT) and the deleted region (A followed by the respective numbers of the sgRNAs couple) shows the exact position of the Sa Cas9 (i.e. between nucleotide $N_3$ and $N_4$ of the proto spacer).

Figure 6:
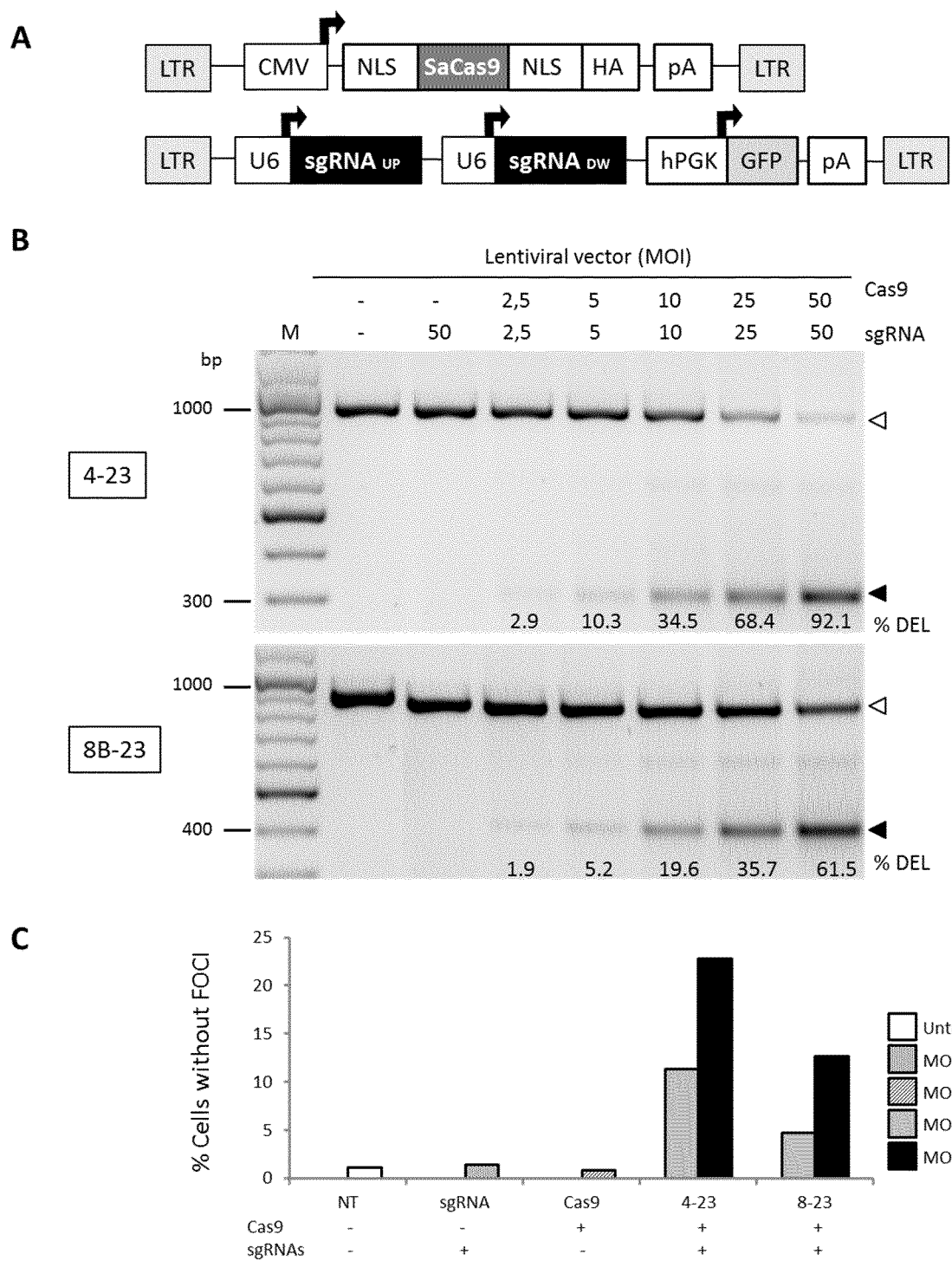

FIG. 6. Deletion of DMPK CTG repeat and foci disappearance in DM1 cells treated with lentiviral vectors CRISPR-Cas9. A) Schematic representation for the dual system of lentiviral vectors Cas9 and sgRNAs from *Staphylococcus aureus* (Sa) under the expression of CMV and U6 promoters, respectively. sgRNAs UP and DW: sgRNAs targeting the genomic region upstream and downstream the CTG repeat. LTR: long terminal repeat; CMV: cytomegalovirus promoter; NLS: nuclear localization signal; HA: human influenza hemagglutinin epitope; pA: polyadenylation signal; U6: human promoter of small nuclear RNA; hPGK: human phosphoglycerate kinase promoter; GFP: enhanced green fluorescent protein. B) Detection of the CTG repeat excision in DM1 immortalized myoblasts by genomic PCR. Cells from patient harboring 2600 CTG repeats have been transduced with increasing MOI of lentiviral vectors Cas9 and sgRNAs (couples 4-23 and 8B-23, as indicated on the left of each agaro se gel image). Edited and unedited PCR amplicons are indicated by a black and a white arrow, respectively. Estimation of the percentage of CTG repeat deletion is indicated below the corresponding PCR band (# % DEL). C) Quantification of DM1 cells which have lost the nuclear foci after treatment with lentiviral vectors CRISPR-Cas9.

FIG. 7. Detection of the genomic excision of the CTG repeat expansion in DM1 myoblasts. A) Map of DMPK gene indicating the relative position of EcoRI restriction sites, Alu polymorphism, CTG repeats [(CTG)n], stop codon of the gene (stop) and Cas9 cutting position for sgRNA targets 4 and 23 (Cut UP and DW) upstream and downstream the CTG repeat. Probe used for the southern blot spans the region from exon 13 to 15. B) Southern blot image for DNA extracted from the indicated myoblasts, digested with EcoRI and hybridized with the radioactive probe depicted above. WT and DM1: immortalized wild type and DM1 myoblasts with (+) or without (−) lentiviral vectors Cas9 and sgRNA. Ctrl 1 and 2: DM1 control clones with 2600 CTG repeat expansion; Delta: DM1 clone harboring deletion of the CTG repeat in both alleles, with and without CTG expansion. Asterisk: EcoRI fragment with 2600 CTG repeats. C) Table indicating the number of CTG repeats [(CTG)n] for each cell type (WT, DM1 and DM1 Delta), for each of the two alleles (1 and 2), and respective expected size for EcoRI-digested genomic DNA bands. In both myoblasts, WT and DM1, one of the two alleles (here indicted as 1) carries the Alu polymorphism which is ~1 Kb in length.

Figure 8:
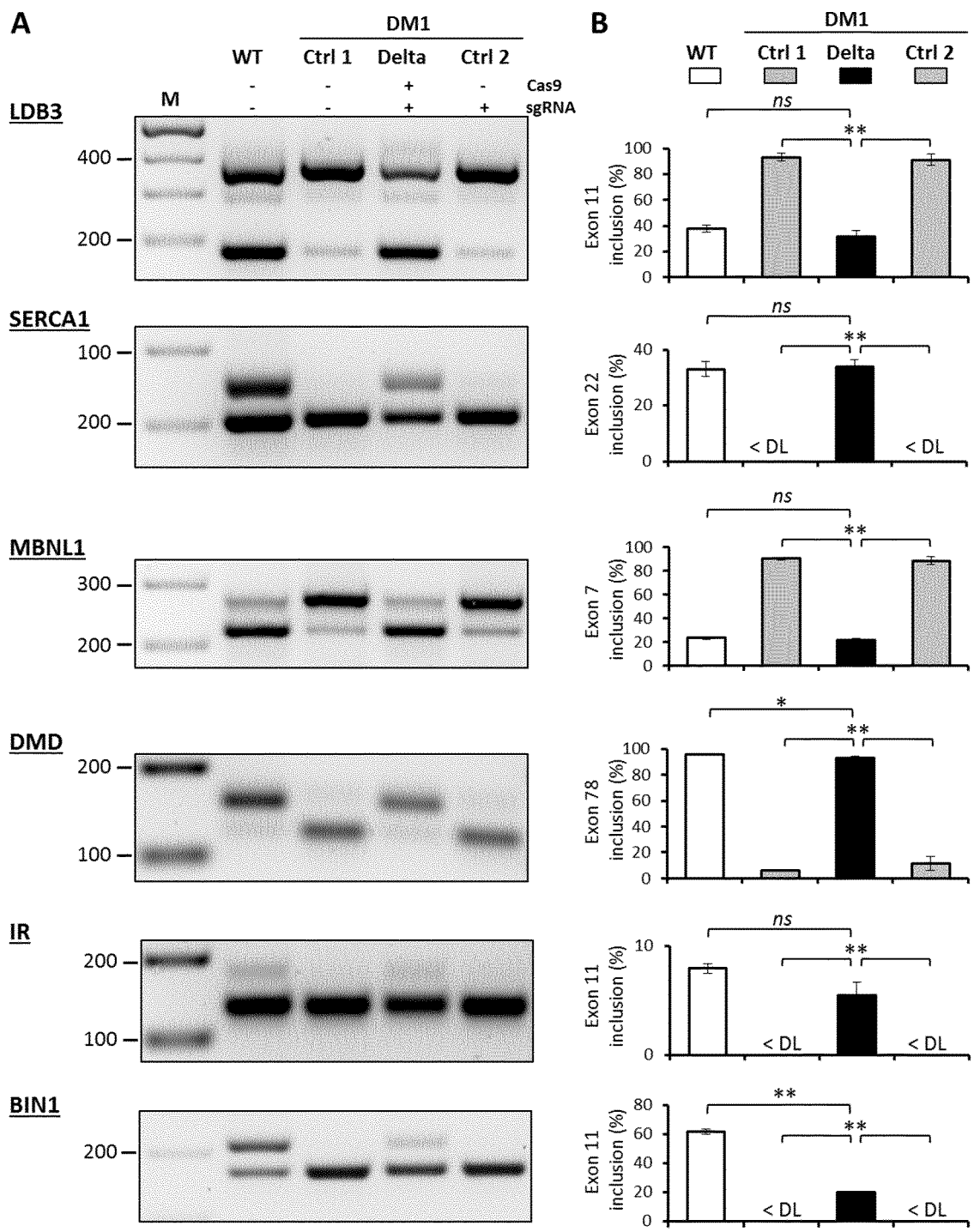

FIG. 8. Deletion of CTG repeat expansion reverts DM1 splicing anomalies. Splicing profiles of the indicated transcripts in differentiated myoblasts wild type (WT) and DM1, with (ctrl 1 and 2) and without (Delta) CTG repeat expansion. (A) Agarose gel images of the RT-PCR and (B) their respective quantification. Histograms are the average of three independent biological replicates ±standard deviation. Statistical analysis by student T-Test: bimodal and unequal variance. *: $P<0.05$; **: $P<0.01$; ns: not significant; DL: below detection limit.

Figure 9:
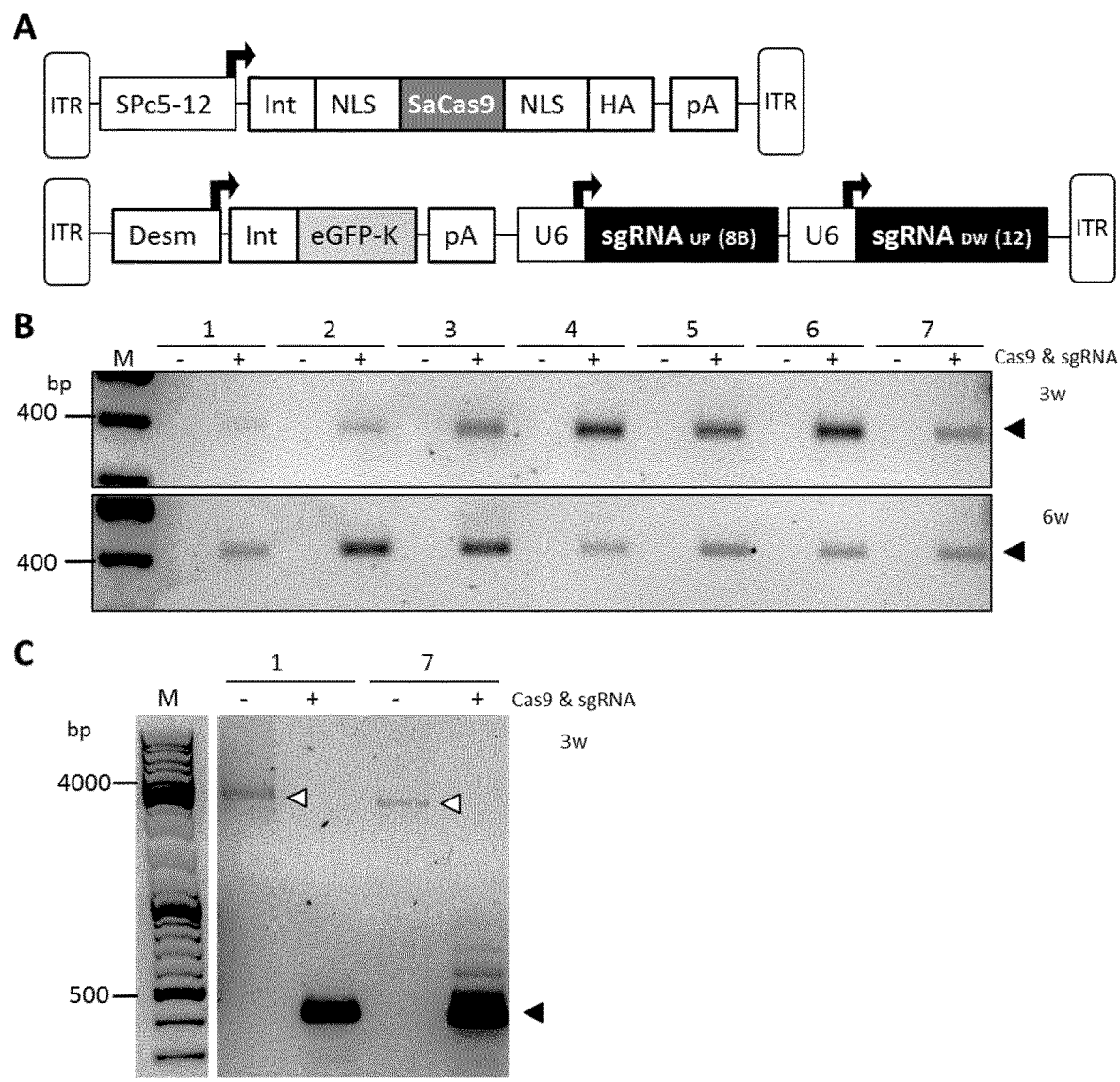

FIG. 9. In vivo deletion of DMPK CTG repeat expansion in heterozygous DMSXL mice by AAV-CRISPR. A) AAVs for SaCas9 and sgRNAs under the expression of SPc5-12 and U6 promoters, respectively. ITR: Inverted Terminal Repeat; SPc5-12: synthetic muscle-specific promoter; Int: intron; NLS: nuclear localization signal; HA: human influenza hemagglutinin epitope; pA: polyadenylation signal; Desm: Desmin promoter; eGFP-K=enhanced Green Fluorescent Protein linked to Kash peptide; U6: human promoter of small nuclear RNA; sgRNAs UP and DW: sgRNAs targeting the genomic region upstream and downstream the CTG repeat. B) Genomic PCR showing CTG repeat excision in heterozygous DMSXL mice subject to intramuscular injection of AAV vectors Cas9 and sgRNAs. Equal number of viral particles of AAVs Cas9 and sgRNA have been co-injected into the left TA (+): $0.6*10^{11}$ and $1*10^{11}$ total Vg, at 3 and 6 weeks of age (3-6 w), respectively. PBS was injected as negative control into the right TA (−). C) Genomic PCR showing undeleted PCR product. Black arrow: deleted PCR product (399 bp). White arrow: undeleted PCR products with ~1200 CTG repeat (~4527 bp).

DETAILED DESCRIPTION OF THE INVENTION

The inventors herein show that the CRISPR-Cas9 system derived from *S. aureus* may be efficiently used to excise nucleotide repeats from the DMPK gene, thereby providing a powerful tool for the treatment of Myotonic Dystrophy type 1 (DM1).

Accordingly, in a first aspect it is herein disclosed
(i) a first sgRNA molecule which is able to bind by base-pairing the sequence complementary to a target sequence (protospacer) in genomic DNA which is located 5' from a nucleotide repeat located within the 3'UTR of the DMPK gene.
(ii) a second sgRNA molecule which is able to bind by base-pairing the sequence complementary to a target sequence (protospacer) in the genomic DNA which is located 3' from a nucleotide repeat located within the 3'UTR of the DMPK gene.
(iii) a pair of sgRNA molecules that are each able to bind by base-pairing sequences complementary to the target sequences in the genomic DNA which are located 5' and 3', respectively, from a nucleotide repeat located within the 3'-UTR of the DMPK gene.

CRISPR-Cas9 System

The Clustered Regularly Interspaced Short Palindromic Repeats (CRISPR) Type II system is a RNA-guided endonuclease technology that has recently emerged as a promising genome editing tool. There are two distinct components to this system: (1) a guide RNA and (2) an endonuclease, in this case the CRISPR associated (Cas) nuclease, Cas9. The guide RNA is a combination of bacterial CRISPR RNA (crRNA) and a trans-activating crRNA (tracrRNA) engineered into a single chimeric guide RNA (sgRNA) transcript (Jinek et al., Science 2012 Aug. 7; 337(6096):816-21). The sgRNA combines the targeting specificity of the crRNA with the scaffolding properties of the tracrRNA into a single transcript. When the sgRNA and the Cas9 are expressed in the cell, the genomic target sequence can be modified or permanently disrupted.

The sgRNA/Cas9 complex is recruited to the target sequence by the base-pairing between the sgRNA guide sequence and the complement to the target sequence in the genomic DNA (protospacer). For successful binding of Cas9, the genomic target sequence must also contain the correct Protospacer Adjacent Motif (PAM) sequence immediately following the target sequence. The binding of the sgRNA/Cas9 complex localizes the Cas9 to the genomic target sequence so that the Cas9 endonuclease can cut both strands of DNA causing a Double Strand Break (DSB). Cas9 will cut between the $3^{rd}$ and $4^{th}$ nucleotides upstream of the PAM sequence. According to the system implemented in the present invention, the DSB can then be repaired through the Non-Homologous End Joining (NHEJ) repair pathway.

The present invention relates to the implementation of this powerful system which is herein improved in an innovative way, for efficiently excising repeat sequences that have been reported to be associated with Myotonic Dystrophy type 1 (DM1).

Cas9 Endonuclease

The DNA-targeting mechanisms of the type II CRISPR-Cas system involves a guide RNA which directs the Cas9 endonuclease to cleave the targeted DNA in a sequence-specific manner, dependent on the presence of a Protospacer Adjacent Motif (PAM) on the targeted DNA.

The PAM sequence varies depending on the species of the bacteria from which the Cas9 endonuclease was derived.

In the context of the present invention, the Cas9 endonuclease is derived from *S. aureus* (SaCas9). Therefore, the cleavage of the DNA is dependent on the presence of the PAM specific to SaCas9. The consensus PAM sequence for SaCas9 is NNGRRT, with R=A or G (AYYCNN in the complementary strand, with Y=T or C) (Ran FA et al, Nature 2015; Kleinstiver B P et al, Nat Biotech 2015).

The Cas9 endonuclease used in the present invention may also be a SaCas9 endonuclease functional variant.

By "functional variant" it is meant a variant Cas9 endonuclease having a sequence different from a parent SaCas9 endonuclease, able to induce site-directed double strand breaks in DNA, by recognizing the same Protospacer Adjacent Motif (PAM) as the parent SaCas9 and matching to the same constant moiety of the sgRNA. Said variant may be derived from a parent SaCas9 endonuclease, such as the SaCas9 having GenBank ID CCK74173.1 or encoded by Addgene plasmid 61591 (with an amino acid sequence as shown in SEQ ID NO:42). For example, the functional variant SaCas9 endonuclease may comprise one or more amino acid insertions, deletions or substitutions as compared to a known SaCas9 endonuclease, and may be at least 50%, 60%, 70%, 80%, 90%, 95%, 96%, 97%, 98% or 99% identical to a known SaCas9 endonuclease.

Guide-RNAs

It is herein disclosed single guide RNAs (or sgRNAs) that are specifically designed for the excision of trinucleotide repeat expansion from DMPK, using Cas9 endonuclease derived from *S. aureus*, or a variant of Cas9 endonuclease derived from *S. aureus*.

As mentioned above, the sgRNA is the part of the CRISPR-Cas9 system that provides genomic DNA targeting specificity to the system. The targeted genomic DNA sequence comprises from 15 to 40 nucleotides, in particular from 20 to 30 nucleotides, in particular from 20 to 25 nucleotides, such as 20, 21, 22, 23, 24, 25 nucleotides followed by an appropriate Protospacer Adjacent Motif (PAM) as described above. In a particular embodiment, the sgRNA molecule comprises a guide RNA sequence which is complementary to the complement sequence of a genomic sequence from 15 to 40 nucleotides, in particular from 20 to 30 nucleotides, in particular from 20 to 25 nucleotides, such as 20, 21, 22, 23, 24, 25 nucleotides, more specifically to 21 or 24 nucleotides, preceding a PAM within the 3'-UTR of the DMPK gene.

In a particular embodiment, the guide RNA sequence is either identical or at least 80% identical, preferably at least 85%, 90%, 95%, 96%, 97%, 98%, or at least 99% identical to said genomic sequence of DMPK and is able to hybridize the complement sequence of said genomic sequence from 15 to 40 nucleotides, in particular from 20 to 30 nucleotides, in particular from 20 to 25 nucleotides, such as 20, 21, 22, 23, 24, 25 nucleotides, more specifically to 21 or 24 nucleotides, preceding the PAM specific to SaCas9. As it is well known by those skilled in the art, the sgRNA does not contain the PAM motif and as a consequence does not bind to the sequence complementary to the PAM. The target sequence may be on either strand of the genomic DNA, within the 3'-UTR of the DMPK gene. Therefore, according to the present invention, the entire target sequence and the PAM are in the 3'-UTR of the DMPK gene.

In the context of the present invention, the "3'-UTR" is defined as the genomic region that goes from the stop codon of the DMPK gene to the polyadenylation of the DMPK gene.

Bioinformatics tools are available for identifying target genomic DNA sequences comprising the appropriate PAM such as those provided by the following web tools: CRISPR Design (crispr.mit.edu), E-CRISP, (Worldwide Web site: e-crisp.org/E-CRISP/designcrispr.html), CasFinder (arep.med.harvard.edu/CasFinder/), and CRISPOR (tefor.net/crispor/crispor.cgi). A person skilled in the art can also refer to Doench et al., Nat Biotechnol. 2014 December; 32(12):1262-7 or Prykhozhij et al., PLoS One. 2015 Mar. 5; 10(3):e0119372 and may find further information and resources on the CRISPR-Cas9 system and on identifying target genomic DNA comprising the appropriate PAM on the following website cnb.csic.es/~montoliu/CRISPR/. PAM sequence may alternatively be identified by using such a sequence as a query in sequence alignment tools, such as the BLAST or FASTA algorithm, within a gene of interest.

Yet, in the present application, the inventors show that only a limited number of sgRNA among those targeting a region downstream of the nucleotide repeat in the DMPK gene is able to provide efficient excision of such repeat.

As is well known, a sgRNA is a fusion of a crRNA and a tracrRNA which provides both targeting specificity (that is conferred by the guide sequence base-pairing to the complement sequence of the target genomic DNA sequence) and scaffolding/binding ability for a Cas9 endonuclease. In other words, a sgRNA molecule includes a guide sequence (corresponding to the specific part of crRNA that binds to the complement of proto spacer) and a sgRNA constant moiety (comprising the unspecific part of the crRNA, a linker loop and the tracrRNA). The sgRNA constant moiety and the selected Cas9 endonuclease match, in the sense that both are derived from *S. aureus*.

In a particular embodiment, the constant sequence of the sgRNA is the Sa sgRNA constant moiety as shown in SEQ ID NO: 6 (sequence of 81 nucleotides, derived from Addgene plasmid 61591).

SEQ ID NO: 6:
GUUUUAGUACUCUGGAAACAGAAUCUACUAAAACAAGGCAAAAUGCCGUG
UUUAUCUCGUCAACUUGUUGGCGAGAUUUUU

In another embodiment, the constant sequence of the sgRNA is a functional variant of the Sa sgRNA constant moiety shown in SEQ ID NO:6, having at least 60%, 70%, 80%, 85%, 90%, 95%, 96%, 97%, 98% or 99% identity with the sequence shown in SEQ ID NO:6 and being able to provide scaffolding/binding ability for a SaCas9 endonuclease or for a functional variant of a SaCas9 endonuclease.

Molecular biology kits and tools, such as appropriate plasmids, are available for easily produce a sgRNA of the desired specificity in terms of both the targeted genomic DNA sequence of DMPK and the SaCas9 endonuclease. For example, a number of plasmids and tools are available from Addgene. In a particular embodiment, the sgRNA or the sgRNA pair is expressed from a plasmid under the control of an U6 promoter. In a particular embodiment, both sgRNAs of the sgRNA pair of the invention are expressed from a single expression cassette containing the two sgRNA scaffolds, each one under the control of a promoter, in particular the U6 promoter, in the same vector (for example in the same plasmid or in the same recombinant viral genome such as in an AAV genome or a lentiviral genome). In a particular embodiment, the two sgRNA scaffolds are provided in reverse position (or tail to tail orientation) or in tandem, in particular in tandem (e.g. head to tail orientation). In another embodiment, the SaCas9 endonuclease coding gene is operably linked to a promoter such as an inducible or constitutive promoter, in particular an ubiquitous or tissue-specific promoter, in particular a muscle-specific promoter. Ubiquitous promoters include, for example, the EFS, CMV, SFFV or CAG promoter. Muscle-specific promoters include, without limitation, the muscle creatine kinase (MCK) promoter, the desmin promoter or the synthetic C5.12 promoter as is well known in the art. In addition, the promoter used for expression of the SaCas9 endonuclease may be an inducible promoter such as a tetracycline-, tamoxifen- or ecdysone-inducible promoter.

The first and second sgRNA molecules are each complementary to a region which is 5' and 3' from the nucleotide repeat expansion of DMPK to be excised, respectively. The sgRNA molecules are thus designed to bind specifically regions upstream and downstream of the nucleotide repeat expansion with the PAM, wherein the entire target sequence and the PAM are within the 3'UTR of the DMPK gene.

Distance of the targeted sequence (region of homology+PAM) from the excised region may not be critical, but in order to minimize the destabilization of the gene structure, the targeted sequence may be selected to be within less than 500, 400, 300, 200, 100, 90, 80, 70, 60, 50, 40, 30, 20 or less than 10 nucleotide from the closest extremity of the nucleotide repeat expansion. For example, considering the sgRNA which is designed to direct induction of a DSB 5' from the nucleotide repeat expansion, the most 3' nucleotide of the PAM of the targeted sequence is within less than 500, 400, 300, 200, 100, 90, 80, 70, 60, 50, 40, 30, 20 or less than 10 nucleotide from the most 5' nucleotide of the first (considering the 5' to 3' direction) nucleotide of the nucleotide repeat expansion to be excised.

The sgRNA molecules are designed for excising a trinucleotide repeat expansion located within the 3'-untranslated region of the DMPK gene, using SaCas9. In a particular variant of this embodiment, the invention relates to a sgRNA molecule comprising a guide sequence of 15-40 nucleotides comprising a sequence selected in the group consisting of:

AGUCGAAGACAGUUC (SEQ ID NO: 7)

ACAACCGCUCCGAGC (SEQ ID NO: 8)

GGCGAACGGGGCUCG (SEQ ID NO: 9)

AGGGUCCUUGUAGCC (SEQ ID NO: 10)

AAUACCGAGGAAUGU. (SEQ ID NO: 11)

In a more particular embodiment, the invention relates to a sgRNA molecule comprising a guide sequence selected in the group consisting of:

GCCCCGGAGUCGAAGACAGUUC (SEQ ID NO: 1)

CAGUUCACAACCGCUCCGAGC (SEQ ID NO: 2)

GCGGCCGGCGAACGGGGCUCG (SEQ ID NO: 3)

GGCUCGAAGGGUCCUUGUAGCC (SEQ ID NO: 4)

GACAAUAAAUACCGAGGAAUGU. (SEQ ID NO: 5)

In a more particular embodiment, the invention relates to a sgRNA molecule comprising a guide sequence selected in the group consisting of:

GCCCCGGAGUCGAAGACAGUUC (SEQ ID NO: 1)

GCAGUUCACAACCGCUCCGAGC (SEQ ID NO: 18)

GCGGCCGGCGAACGGGGCUCG (SEQ ID NO: 3)

GGCUCGAAGGGUCCUUGUAGCC (SEQ ID NO: 4)

GACAAUAAAUACCGAGGAAUGU. (SEQ ID NO: 5)

In SEQ ID NO:18 as represented above, the underlined G base was introduced as compared to SEQ ID NO:2, because a G is required to start the transcription from the U6 promoter. However, those skilled in the art will understand that other promoters may not require a G in this position immediately preceding the guide coding sequence, or may require one or more other nucleotide bases as is well known in the art.

The invention further relates to a vector as defined above, comprising a sequence coding a sgRNA molecule comprising a guide sequence selected from the group consisting of SEQ ID NO:1 to 5 and SEQ ID NO: 18. In a further particular embodiment, the sequence coding a sgRNA molecule further comprises a sequence coding a sgRNA constant moiety sequence as shown in SEQ ID NO:6, or a functional variant thereof as defined above. More particularly, the sequence coding the entire sgRNA molecule is selected from the group consisting of SEQ ID NO:12 to 16.

In a particular embodiment, the pair of sgRNA molecules is a pair of sgRNAs comprising:

a first sgRNA molecule used for inducing double strand break (DSB) upstream (or 5') of the trinucleotide repeat expansion region located within the 3'UTR of the DMPK gene, wherein the upstream DSB is induced within the 3'-UTR;

a second sgRNA molecule used for inducing DSB downstream (or 3') of the trinucleotide repeat expansion region of DMPK, wherein the downstream DSB is induced within the 3'-UTR, wherein the second sgRNA molecule comprises a guide sequence ranging from 15-40 nucleotides in length, in particular from 20 to 30 nucleotides, in particular from 20 to 25 nucleotides, such as consisting of 20, 21, 22, 23, 24 or 25 nucleotides, in particular 21 or 24 nucleotides, and comprising the sequence shown in SEQ ID NO:11.

In a more particular embodiment, the first sgRNA molecule comprises a guide sequence ranging from 15-40 nucleotides in length, in particular from 20 to 30 nucleotides, in particular from 20 to 25 nucleotides, such as consisting of 20, 21, 22, 23, 24 or 25 nucleotides, in particular 21 or 24 nucleotides, and comprising a sequence selected from SEQ ID NO:7 to SEQ ID NO:10. In a preferred embodiment, the guide sequence of the first sgRNA consists of a nucleotide sequence selected from SEQ ID NO:1 to SEQ ID NO:4 and SEQ ID NO:18.

In another preferred embodiment, the guide sequence of the second sgRNA consists of a nucleotide sequence as shown in SEQ ID NO:5.

In another embodiment, the pair of sgRNA molecules of the invention comprises a pair of guide sequence selected in the group consisting of:
SEQ ID NO:1 and SEQ ID NO:5;
SEQ ID NO:2 (or SEQ ID NO:18) and SEQ ID NO:5;
SEQ ID NO:3 and SEQ ID NO:5;
SEQ ID NO:4 and SEQ ID NO:5;

As mentioned above, the sgRNA of the invention may be expressed from an expression cassette. Expression of the sgRNA may in particular be controlled by a promoter such as a U6 promoter. Accordingly, the invention also includes a cassette for expression of a sgRNA, comprising a sgRNA coding sequence placed under the control of a promoter such as the U6 promoter shown in SEQ ID NO:17.

In a particular embodiment, the expression cassette comprises the following sequence for expression of the sgRNA from a U6 promoter:
the combination, in the 5' to 3' orientation, of SEQ ID NO:17, SEQ ID NO:43 and SEQ ID NO:48;
the combination, in the 5' to 3' orientation, of SEQ ID NO:17, SEQ ID NO:44 and SEQ ID NO:48;
the combination, in the 5' to 3' orientation, of SEQ ID NO:17, SEQ ID NO:45 and SEQ ID NO:48;
the combination, in the 5' to 3' orientation, of SEQ ID NO:17, SEQ ID NO:46 and SEQ ID NO:48; or
the combination, in the 5' to 3' orientation, of SEQ ID NO:17, SEQ ID NO:47 and SEQ ID NO:48.

Methods and Uses of the Invention

The present invention contemplates various ways of reaching the target genomic DNA sequence of DMPK with a SaCas9 endonuclease and sgRNA molecules. In some embodiments, the SaCas9 endonuclease is introduced within a cell in a polypeptide form. In a variant, the SaCas9 endonuclease is conjugated to or fused to a cell penetrating peptide, which is a peptide that facilitates the uptake of a molecule into a cell. The sgRNA molecules may also be administered to the cell as isolated oligonucleotide, either directly or using transfection reagents such as lipidic derivatives, liposomes, calcium phosphate, nanoparticles, microinjection or electroporation. The SaCas9 endonuclease and sgRNA molecules may also be pre-assembled in vitro as ribonucleoprotein complex and then delivered to the cells either directly or using transfection reagents.

In another embodiment, the present invention contemplates introducing the SaCas9 endonuclease and/or sgRNA molecules into the target cell in the form of a vector expressing said endonuclease and/or sgRNA molecules. The invention thus also relates to a vector encoding the sgRNA molecule or the pair of sgRNA molecules according to the invention. Methods of introducing and expressing genes into a cell are known in the art. The expression vector can be transferred into a host cell by physical, chemical, or biological means. The expression vector may be introduced in the cell using known physical methods such as calcium phosphate precipitation, lipofection, particle bombardment, microinjection, electroporation. Chemical means for introducing a polynucleotide into a host cell include colloidal dispersion systems, such as macromolecule complexes, nanocapsules, microspheres, beads, and lipid derivatives and liposomes. In other embodiments, the SaCas9 endonuclease and/or the sgRNA molecules are introducing by biological means, in particular by a viral vector. Representative viral vectors useful in the practice of the invention include, without limitation, a vector derived from adenovirus, retrovirus, in particular lentivirus, poxviruses, herpes simplex virus I and adeno-associated virus (AAV). Selection of the appropriate viral vector will of course depend on the targeted cell and the virus tropism.

In an embodiment, the SaCas9 endonuclease and the sgRNA molecules are provided within different vectors (such as two vectors, one containing a gene coding the SaCas9 endonuclease, and a second coding both sgRNA molecules; or three vectors, one coding the SaCas9 endonuclease and one vector for each sgRNA molecule). In another embodiment, all the elements of the CRISPR-Cas9 system, including the SaCas9 endonuclease and both sgRNA molecules required for excision of the trinucleotide repeat expansion from DMPK, are expressed from a single expression vector.

In a particular embodiment, the SaCas9 endonuclease and the sgRNA molecules of the invention are used in combination with other DM1 treatments, simultaneously or sequentially. In particular, the SaCas9 endonuclease and the sgRNA molecules of the invention may be used simultaneously or sequentially in combination with another pair of sgRNA molecules and another or the same Cas9 endonuclease, to excise the repeat expansion.

In a particular embodiment, the other pair of sgRNA molecules is selected from the pairs disclosed in EP16306426 (which is incorporated by reference in its entirety).

In a particular embodiment, the other pair of sgRNA molecules comprises a sgRNA molecule comprising a guide sequence of 15-40 nucleotides comprising the nucleotide sequence shown in SEQ ID NO:12 of EP16306426.

In another particular embodiment, the other pair of sgRNA molecules comprises a first sgRNA molecule, which comprises a guide sequence of 15-40 nucleotides in length comprising the nucleotide sequence shown in SEQ ID NO:8 of EP16306426, SEQ ID NO:9 of EP16306426, SEQ ID NO:10 of EP16306426 or SEQ ID NO:11 of EP16306426.

In another particular embodiment, the other pair of sgRNA molecules comprises a first sgRNA molecule, wherein the guide sequence of the first sgRNA consists of a nucleotide sequence selected from SEQ ID NO:1-4 of EP16306426 and SEQ ID NO:20 of EP16306426. In another particular embodiment, the other pair of sgRNA molecules comprises a second sgRNA molecule, wherein the guide sequence of the second sgRNA molecule consists of a nucleotide sequence selected from SEQ ID NO:5 of EP16306426, SEQ ID NO:6 of EP16306426 and SEQ ID NO:21 of EP16306426.

In an aspect, the invention also relates to a target cell comprising a sgRNA molecule of the invention or a sgRNA pair of the invention, or which is transfected or transduced with a vector of the invention. Optionally, the target cell further expresses a SaCas9 endonuclease, for example from the same vector as the vector expressing the sgRNA molecule or the sgRNA pair of the invention. For example, the recombinant cell may be selected from an iPS-derived mesenchymal progenitor cells (MPCs), or a hESC-derived MPCs .

The system of the present invention is used for excising a nucleotide repeat expansion, in particular a trinucleotide repeat, within the 3' untranslated region of the DMPK gene. In a particular embodiment, the nucleotide repeat expansion (e.g. a trinucleotide repeat expansion) comprises from 20 to 10000 repeats of the nucleotide motif, more particularly from 50 to 5000 repeats. For example, the nucleotide repeat expansion to be excised (e.g. a trinucleotide repeat expansion) may comprise any number of repeats, such as at least 20, 30, 40, 50, 60, 70, 80, 90, 100, 200, 300, 400, 500, 600, 700, 800, 900, 1000 or at least more than 2000 repeats of the nucleotide motif. More specifically, the number of repeats is a pathological number of repeats, which means that said nucleotide repeat (e.g. a trinucleotide repeat) is associated, or may be associated, to a disease state. In a particular embodiment, the repeat is a CTG repeat within the 3'-untranslated region of the DMPK gene and is pathological from 20 or more repeats or from 50 or more repeats. In a particular embodiment, the nucleotide repeat expansion comprises from 20 to 10000 repeats, more particularly from 50 to 5000 repeats. In particular, the nucleotide repeat expansion comprises from 1000 to 3000 repeats, more particularly from 1200 to 2600 repeats.

As used herein, the term "treating" and "treatment" refers to administering to a subject an effective amount of a composition so that the subject has a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Alternatively, treatment is "effective" if the progression of a disease is reduced or halted. "Treatment" can also mean prolonging survival as compared to expected survival if not receiving treatment. Those in need of treatment include those already diagnosed with a disorder associated with expression of a polynucleotide sequence, as well as those likely to develop such a disorder due to genetic susceptibility or other factors. As used herein, the term "treating" and "treatment" also refers the prevention of a disease or disorder, which means delaying or preventing the onset of such disease or disorder.

The present invention provides the treatment of a nucleotide repeat expansion disorder which is DM1, associated with a trinucleotide (such as a CTG) repeat expansion within the 3'-untranslated region of the DMPK gene.

The present invention also relates to a pair of sgRNA molecules as described above for use as a medicament.

The invention further relates to a pair of sgRNA molecules as described above for use in a method for treating DM1.

The invention further relates to the use of a pair of sgRNA molecules as described above for the manufacture of a medicament for the treatment of DM1.

The invention further relates to a method for treating DM1, comprising administering to a subject in need thereof an effective amount of the pair of sgRNA molecules as described above.

The sgRNA molecule, the pair of sgRNA molecules, the recombinant SaCas9 endonuclease protein, the vector (either coding one or more sgRNA molecule and/or a SaCas9 endonuclease) and the cell according to the invention can be formulated and administered to treat myotonic dystrophy, by any means that produces contact of the sgRNA molecule, the pair of sgRNA molecules, the vector and the cell with its site of action in the subject in need thereof.

The present invention also provides pharmaceutical compositions comprising a sgRNA or sgRNA pair of the invention, or the recombinant SaCas9 endonuclease protein or the vector of the invention (coding either a sgRNA of the invention, or a pair of sgRNAs alone or together with a SaCas9 endonuclease coding sequence), or the cell of the invention. Such compositions comprise a therapeutically effective amount of the therapeutic (the sgRNA(s), vector or cell of the invention), and a pharmaceutically acceptable carrier. In a specific embodiment, the term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject.

The pharmaceutical composition is adapted for any type of administration to a mammal, in particular a human being and is formulated in accordance with routine procedures. The composition is formulated by using suitable conventional pharmaceutical carrier, diluent and/or excipient. Administration of the composition may be via any common route so long as the target tissue is available via that route. This includes for example oral, nasal, intradermal, subcutaneous, intramuscular, intraperitoneal or intravenous administration. Preferably, the composition is formulated as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to, ease pain at the, site of the injection.

The amount of the therapeutic of the invention which will be effective in the treatment of a nucleotide repeat expansion can be determined by standard clinical techniques. In addition, in vivo and/or in vitro assays may optionally be employed to help predict optimal dosage ranges. The precise dose to be employed in the formulation will also depend on the route of administration, and the seriousness of the disease, and should be decided according to the judgment of the practitioner and each patient's circumstances. The dosage of the sgRNA(s), the vector or the cell administered to the subject in need thereof will vary based on several factors including, without limitation, the route of administration, the subject's age or the level of expression necessary to obtain the required the therapeutic effect. One skilled in the art can readily determine, based on its knowledge in this field, the dosage range required based on these factors and others.

EXAMPLES

Below is provided a table matching SEQ ID NOs with sgRNA numbers used in the following experimental part and in figures.

| sgRNA number | 1 | 4 | 7 | 8B | 23 |
|---|---|---|---|---|---|
| SEQ ID NO | 1 | 18 | 3 | 4 | 5 |

Materials and Methods
Plasmids Construction

Plasmid encoding for *S. aureus* Cas9 derives from plasmid pX601-AAV-CMV::NLS-SaCas9-NLS-3xHA-bGHpA; U6::BsaI-sgRNA (MLS42) [Ran et al, 2015]. EFS promoter was PCR amplified with primers F-XhoI-MreI-EFS (MLS63) and R-XmaI-NruI-EFS (MLS64) and cloned into XhoI/AgeI site of promoterless pX601-AAV-::NLS-SaCas9-NLS-3xHA-bGHpA; U6::BsaI-sgRNA to obtain pAAV-EFS::NLS-SaCas9-NLS-3xHA-bGHpA; U6::BsaI-sgRNA (MLS43).

Second cassette for sgRNA (U6::BbsI-sgRNA) was cloned in tandem into Acc65I site of plasmid MLS43, upstream the first sgRNA cassette, to obtain the construct pAAV-EFS::NLS-SaCas9-NLS-3xHA-bGHpA; U6::BbsI-sgRNA; U6::BsaI-sgRNA (MLS47). Insert U6::BbsI-sgRNA was synthetically synthesized (GeneCust) using the same sequence of the existing cassette U6::BsaI-sgRNA but exchanging into BbsI the sgRNA protospacer cloning site. Sa sgRNA protospacers, with n ID number, have been synthesized as couple of oligonucleotides forward and reverse (Tab. 2) and in vitro annealed prior their cloning into restriction sites BbsI (MLS47 derivative plasmids pAAV-EFS::NLS-SaCas9-NLS-3xHA-bGHpA; U6::n-DMPK-sgRNA; U6::BsaI-sgRNA) and BsaI (plasmids pAAV-EFS::NLS-SaCas9-NLS-3xHA-bGHpA; U6::n-sgRNA; U6::n-sgRNA_DMPK). Lentiviral vectors were constructed by using the backbone of a pCCL plasmid [pCC-hPGK.GFP (MLS87); generous concession from Dr. Mario Amendola]. Inserts U6::4-sgRNA; U6::23-sgRNA_DMPK and U6::8B-sgRNA; U6::23-sgRNA_DMPK (derived from enzymatically digested plasmids MLS93 and MLS95) were cloned into XhoI/EcoRV site of plasmid MLS87 to obtain pCCL-U6::4-sgRNA; U6::23-sgRNA_DMPK-hPGK.GFP and pCCL-U6::8B-sgRNA; U6::23-sgRNA_DMPK-hPGK.GFP (MLS100 and MLS102). CMV promoter, derived from plasmid MLS42, was cloned into XhoI/AgeI site of promoterless pCCL-GFP (MLS87 without hPGK promoter) to obtain pCCL-CMV-GFP (MLS107). Construction of lentiviral vector pCCL-CMV-SaCas9 (MLS110) was done by cloning SaCas9 PCR insert [primers F-AgeI-SaCas9 (MLS142) and R-SalI-SaCas9 (MLS143); plasmid MLS42 as template] into SalI/I/AgeI site of pCCL-CMV (MLS107 without GFP). Adeno associated virus (AAV) vectors for SaCas9 and sgRNA couple 4-23 have been constructed by using pAAV plasmids with sequenced ITR [Genethon plasmid bank]. SaCas9 was PCR amplified with primers F-PmeI-SaCas9 (MLS146) and R-NotI-SaCas9_3xHE (MLS147) and using plasmid MLS42 as template. Gel-purified insert SaCas9 was cloned into PmeI/NotI site of AAV plasmid pC512-Int-smSVpolyA (MLS1) in order to obtain pAAV-SPc5-12-SaCas9 (MLS118). pAAV-Des-eGFP-KASH-U6::4-23-sgRNA_DMPK (MLS123) was obtained by cloning PCR insert U6::4-23-sgRNA_DMPK [primers F-MCS-before-U6SasgRNA (MLS163) and R-PmlI-EndSasgRNA-up (MLS166); plasmid MLS93 as template] into AflII/MssI site of pAAV-Des-EGFP-KASH (MLS23/MLS27).

TABLE 1

List of Plasmids

| Name | Description | Ref |
|---|---|---|
| pX601-AAV-CMV::NLS-SaCas9-NLS-3xHA-bGHpA; U6::BsaI-sgRNA | AAV plasmid carrying *Staphylococcus aureus* (Sa) Cas9 under the control of CMV promoter, and one sgRNA expression cassette (U6::BsaI-sgRNA) under the control of human U6 promoter. | MLS42; Addgene plasmid # 61591; [Ran et al, 2015] |
| pAAV-EFS::NLS-SaCas9-NLS-3xHA-bGHpA; U6::BsaI-sgRNA | Derivative of plasmid MLS42 carrying EFS promoter instead CMV promoter. | MLS43; this study |
| pAAV-EFS::NLS-SaCas9-NLS-3xHA-bGHpA; U6::BbsI-sgRNA; U6::BsaI-sgRNA | Derivative of plasmid MLS43 carrying a second sgRNA expression cassette (U6::BbsI-sgRNA). | MLS47; this study |
| pAAV-EFS::NLS-SaCas9-NLS-3xHA-bGHpA; U6::1-DMPK-sgRNA; U6::BsaI-sgRNA | Derivative of plasmid MLS47 carrying sgRNA 1 protospacer into BbsI site. | MLS51; this study |
| pAAV-EFS::NLS-SaCas9-NLS-3xHA-bGHpA; U6::4-DMPK-sgRNA; U6::BsaI-sgRNA | Derivative of plasmid MLS47 carrying sgRNA 4 protospacer into BbsI site. | MLS52; this study |

TABLE 1-continued

List of Plasmids

| Name | Description | Ref |
|---|---|---|
| pAAV-EFS::NLS-SaCas9-NLS-3xHA-bGHpA; U6::7-DMPK-sgRNA; U6::BsaI-sgRNA | Derivative of plasmid MLS47 carrying sgRNA 7 protospacer into BbsI site. | MLS53; this study |
| pAAV-EFS::NLS-SaCas9-NLS-3xHA-bGHpA; U6::8B-DMPK-sgRNA; U6::BsaI-sgRNA | Derivative of plasmid MLS47 carrying sgRNA 8B protospacer into BbsI site. | MLS54; this study |
| pAAV-EFS::NLS-SaCas9-NLS-3xHA-bGHpA; U6::10-DMPK-sgRNA; U6::BsaI-sgRNA | Derivative of plasmid MLS47 carrying sgRNA 10 protospacer into BbsI site. | MLS55; this study |
| pAAV-EFS::NLS-SaCas9-NLS-3xHA-bGHpA; U6::15B-DMPK-sgRNA; U6::BsaI-sgRNA | Derivative of plasmid MLS47 carrying sgRNA 15B protospacer into BbsI site. | MES58; this study |
| pAAV-EFS::NLS-SaCas9-NLS-3xHA-bGHpA; U6::17A-DMPK-sgRNA; U6::BsaI-sgRNA | Derivative of plasmid MLS47 carrying sgRNA 17A protospacer into BbsI site. | MLS78; this study |
| pAAV-EFS::NLS-SaCas9-NLS-3xHA-bGHpA; U6::17B-DMPK-sgRNA; U6::BsaI-sgRNA | Derivative of plasmid MLS47 carrying sgRNA 17B protospacer into BbsI site. | MLS79; this study |
| pAAV-EFS::NLS-SaCas9-NLS-3xHA-bGHpA; U6::19-DMPK-sgRNA; U6::BsaI-sgRNA | Derivative of plasmid MLS47 carrying sgRNA 19 protospacer into BbsI site. | MLS80; this study |
| pAAV-EFS::NLS-SaCas9-NLS-3xHA-bGHpA; U6::22-DMPK-sgRNA; U6::BsaI-sgRNA | Derivative of plasmid MLS47 carrying sgRNA 22 protospacer into BbsI site. | MLS59; this study |
| pAAV-EFS::NLS-SaCas9-NLS-3xHA-bGHpA; U6::23-DMPK-sgRNA; U6::BsaI-sgRNA | Derivative of plasmid MLS47 carrying sgRNA 23 protospacer into BbsI site. | MLS81; this study |
| pAAV-EFS::NLS-SaCas9-NLS-3xHA-bGHpA; U6::1-sgRNA; U6::23-sgRNA_DMPK | Derivative of plasmid MLS51 carrying sgRNA 23 protospacer into BsaI site. | MLS92; this study |
| pAAV-EFS::NLS-SaCas9-NLS-3xHA-bGHpA; U6::4-sgRNA; U6::23-sgRNA_DMPK | Derivative of plasmid MLS52 carrying sgRNA 23 protospacer into BsaI site. | MLS93; this study |
| pAAV-EFS::NLS-SaCas9-NLS-3xHA-bGHpA; U6::7-sgRNA; U6::23-sgRNA_DMPK | Derivative of plasmid MLS53 carrying sgRNA 23 protospacer into BsaI site. | MLS94; this study |
| pAAV-EFS::NLS-SaCas9-NLS-3xHA-bGHpA; U6::8B-sgRNA; U6::23sgRNA_DMPK | Derivative of plasmid MLS54 carrying sgRNA 23 protospacer into BsaI site. | MLS95; this study |
| pCCL-hPGK.GFP | pCCL plasmid harboring eGFP under the control of hPGK promoter. | MLS87; Dr. M. Amendola |
| pCCL-CMV-GFP | Derivative of plasmid MLS87 carrying CMV instead hPGK promoter. | MLS107; this study |
| pCCL-CMV-SaCas9 | Derivative of plasmid MLS107 carrying SaCas9 instead eGFP. | MLS110; this study |
| pCCL-U6::4-sgRNA; U6::23-sgRNA_DMPK-hPGK.GFP | Derivative of plasmid MLS87 carrying insert U6::4-sgRNA; U6::23-sgRNA_DMPK from plasmid MLS93. | MLS100; this study |
| pCCL-U6::8B-sgRNA; U6::23-sgRNA_DMPK-hPGK.GFP | Derivative of plasmid MLS87 carrying insert U6::8B-sgRNA; U6::23-sgRNA_DMPK from plasmid MLS95. | MLS102; this study |
| pGG14 | AAV plasmid with SPc5-12 promoter, chimeric intron, MCS and small SV40polyA. | ID_150; Genethon |
| pU7Dtex51AON_long1 | AAV plasmid with sequenced ITRs. | ID_1311; Genethon |
| pC512-Int-smSVpolyA | Derivative of plasmid ID_1311 carrying insert "SPc5-12_Int_MCS_pA" from plasmid ID_150. | MLS1; this study |
| pAAV-SPc5-12-SaCas9 | Derivative of plasmid MLS1 carrying SaCas9 in front of SPc5-12 promoter. | MLS118; this study |
| pAAV-Desmin-MCS | AAV plasmid carrying Desmin promoter, chimeric intron, MCS and polyA. | ID_772; Genethon |
| pBlue-EGFP-KASH | Plasmid carrying synthetically synthesized EGFP-KASH insert (GeneCust) consisting of coding sequence for eGFP with a C-terminus KASH peptide. | MLS22; this study |
| pAAV-Des-EGFP-KASH | Derivative of plasmid ID_772 carrying insert EGFP-KASH from plasmid MLS22. | MLS23; this study |
| pAAV-Des-EGFP-KASH-U6gRNA-NM-1N-DMPK | Derivative of plasmid MLS23 carrying insert U6gRNA-NM-1N-DMPK. | MLS27; this study |
| pAAV-Des-eGFP-KASH-U6::4-23-sgRNA_DMPK | Derivative of plasmid MLS27 with insert U6::4-23-sgRNA_DMPK (from plasmid MLS93) instead insert U6gRNA-NM-1N-DMPK. | MLS123; this study |

TABLE 2

List of Primers

| | Primer name | Sequence from 5' to 3' | Comment | Reference |
|---|---|---|---|---|
| | Constructs Cloning | | | |
| SEQ ID NO: 49 | F-XhoI-MreI-EFS | CGCTCGAGCGCCGGCGTGAGGCTCCG GTGCCCGTCAGTGG | PCR EFS promoter | MLS63; this study |
| SEQ ID NO: 50 | R-XmaI-NruI-EFS | CGCCCGGGTCGCGATCACGACACCTG TGTTCTGGCGGCAAACC | | MLS64; this study |
| SEQ ID NO: 51 | F-AgeI-SaCas9 | GCGACCGGTGCCACCATGGCCCCAAA GAAG | PCR SaCas9 for plasmid pCCL-CMV-SaCas9 | MLS142; this study |
| SEQ ID NO: 52 | R-SalI-SaCas9 | CGCGTCGACCTTAAGCGTAATCTGGA ACATCGTATGGGTAAGCG | | MLS143; this study |
| SEQ ID NO: 53 | F-PmeI-SaCas9 | GCGGTTTAAACGCCACCATGGCCCCA AAGAAG | PCR SaCas9 for plasmid pAAV-SPc5-12-SaCas9 | MLS146; this study |
| SEQ ID NO: 54 | R-NotI-SaCas9_3xHE | CCGCGGCCGCGCGAGCTCTAGGAATT CTTAAGCGTAATC | | MLS147; this study |
| SEQ ID NO: 55 | F-MCS-before-U6SasgRNA | GGAGGTACCTTAAGCAATTGGACATA GTCGTTTAAACC | PCR insert U6::4-23-sgRNA_DMPK for plasmid MLS123 | MLS163; this study |
| SEQ ID NO: 56 | R-PmlI-EndSasgRNA-up | CCTCACGTGTCCTGCGGCCGCAAAAA TCTCG | | MLS166; this study |
| SEQ ID NO: 57 | F_Sa_sgRNA_7_DMPK | CACCGCGGCCGGCGAACGGGGCTCG | Cloning protospacer sgRNA 7 | MLS69; this study |
| SEQ ID NO: 58 | R_Sa_sgRNA_7_DMPK | AAACCGAGCCCCGTTCGCCGGCCGC | | MLS70; this study |
| SEQ ID NO: 59 | F_Sa_sgRNA_8B_DMPK | CACCGGCTCGAAGGGTCCTTGTAGCC | Cloning protospacer sgRNA 8B | MLS67; this study |
| SEQ ID NO: 60 | R_Sa_sgRNA_8B_DMPK | AAACGGCTACAAGGACCCTTCGAGCC | | MLS68; this study |
| SEQ ID NO: 61 | F_Sa_sgRNA_10_DMPK | CACCGCGGCCAGGCTGAGGCCCTGAC | Cloning protospacer sgRNA 10 | MLS75; this study |
| SEQ ID NO: 62 | R_Sa_sgRNA_10_DMPK | AAACGTCAGGGCCTCAGCCTGGCCGC | | MLS76; this study |
| SEQ ID NO: 63 | F_Sa_sgRNA_15B_DMPK | CACCGGGGGGCGCGGGATCCCCGAA AAA | Cloning protospacer sgRNA 15B | MLS81; this study |
| SEQ ID NO: 64 | R_Sa_sgRNA_15B_DMPK | AAACTTTTTCGGGGATCCCGCGCCCC CC | | MLS82; this study |
| SEQ ID NO: 65 | R_Sa_sgRNA_17A_DMPK | CACCGGCTCCGCCCGCTTCGGCGGT | Cloning protospacer sgRNA 17A | MLS128; this study |
| SEQ ID NO: 66 | R_Sa_sgRNA_17A_DMPK | AAACACCGCCGAAGCGGGCGGAGCC | | MLS129; this study |
| SEQ ID NO: 67 | F_Sa_sgRNA_17B_DMPK | CACCGCCGGCTCCGCCCGCTTCGGCG GT | Cloning protospacer sgRNA 17B | MLS130; this study |
| SEQ ID NO: 68 | R_Sa_sgRNA_17B_DMPK | AAACACCGCCGAAGCGGGCGGAGCC GGC | | MLS131; this study |
| SEQ ID NO: 69 | F_Sa_sgRNA_19_DMPK | CACCGAAAACGTGGATTGGGGTTGTT | Cloning protospacer sgRNA 19 | MLS132; this study |
| SEQ ID NO: 70 | R_Sa_sgRNA_19_DMPK | AAACAACAACCCCAATCCACGTTTTC | | MLS133; this study |
| SEQ ID NO: 71 | F_Sa_sgRNA_22_DMPK | CACCGGGGTCTCAGTGCATCCAAAAC | Cloning protospacer sgRNA 22 | ML583; this study |
| SEQ ID NO: 72 | R_Sa_sgRNA_22_DMPK | AAACGTTTTGGATGCACTGAGACCCC | | MLS84; this study |
| SEQ ID NO: 73 | F_Sa_sgRNA_23_DMPK | CACCGACAATAAATACCGAGGAATGT C | loning protospacer sgRNA 23 | MLS134; this study |
| SEQ ID NO: 74 | R_Sa_sgRNA_23_DMPK | AAACACATTCCTCGGTATTTATTGTC | | MLS135; this study |
| | Genomic PCR/Sequencing DMPK 3'-UTR | | | |
| SEQ ID NO: 75 | F1-DMPK-3UTR | GTTCGCCGTTGTTCTGTCTCG | | MLS14; this study |
| SEQ ID NO: 76 | R1-DMPK-3UTR | TCCAGAGCTTTGGGCAGATGG | | MLS15; this study |

TABLE 2-continued

List of Primers

| | Primer name | Sequence from 5' to 3' | Comment | Reference |
|---|---|---|---|---|
| SEQ ID NO: 77 | F1-DMPK-3UTR-KpnI | CCGGGTACCGTTCGCCGTTGTTCTGTCTCG | | MLS34; this study |
| SEQ ID NO: 78 | R1-DMPK-3UTR-XbaI | CCGCTCTAGATCCAGAGCTTTGGGCAGATGG | | MLS35; this study |
| SEQ ID NO: 79 | F2-DMPK-3UTR | GTCCCAGGAGCCAATCAGAGG | | MLS16; this study |
| SEQ ID NO: 80 | R2-DMPK-3UTR | CTAGCTCCTCCCAGACCTTCG | | MLS17; this study |
| | RT-PCR alternative splicing | | | |
| SEQ ID NO: 81 | F-LDB3 | GCAAGACCCTGATGAAGAAGCTC | LDB3 exon 11 | MLS172; Francois et al, 2011 |
| SEQ ID NO: 82 | R-LDB3 | GACAGAAGGCCGGATGCTG | | MLS173; Francois et al, 2011 |
| SEQ ID NO: 83 | F-SERCA1 | ATCTTCAAGCTCCGGGCCCT | SERCA1 exon 22 | MLS174; Kimura et al, 2005 |
| SEQ ID NO: 84 | R-SERCA1 | CAGCTCTGCCTGAAGATGTG | | MLS175; Kimura et al, 2005 |
| SEQ ID NO: 85 | F-MBNL1 | GCTGCCCAATACCAGGTCAAC | MBNL1 exon 7 | MLS170; Arandel et al, 2017 |
| SEQ ID NO: 86 | R-MBNL1 | TGGTGGGAGAAATGCTGTATGC | | MLS171; Arandel et al, 2017 |
| SEQ ID NO: 87 | F-DMD | TTAGAGGAGGTGATGGAGCA | DMD exon 78 | MLS176; Rau et al, 2015 |
| SEQ ID NO: 88 | R-DMD | GATACTAAGGACTCCATCGC | | MLS177; Rau et al, 2015 |
| SEQ ID NO: 89 | F-IR-ex10-12 | CCAAAGACAGACTCTCAGAT | IR exon 11 | MLS178; Savkur et al 2001 |
| SEQ ID NO: 90 | R-IR-ex10-12 | AACATCGCCAAGGGACCTGC | | MLS179; Savkur et al 2001 |
| SEQ ID NO: 91 | F-BIN1 | AGAACCTCAATGATGTGCTGG | BIN1 exon 11 | MLS168; Fugier et al 2011 |
| SEQ ID NO: 92 | R-BIN1 | TCGTGTTGACTCTGATCTCGG | | MLS169; Fugier et al 2011 |

Design of sgRNAs

All possible SaCas9 targets within the DMPK 3'-UTR were screened manually and by programs CasBLASTR (see Worldwide Web site: casblastr.org/) and CRISPOR (tefor.net/crispor). PAM sequence NNGRRT was used for the screening, with R=A or G (AYYCNN in the non-coding strand, with Y=T or C) [Ran et al, Nature 2015; Kleinstiver et al, Nat Biotech 2015].

For each sgRNA protospacer, number of potential off-targets was calculated by program CasOFFinder (see Worldwide Web site: rgenome.net/cas-offinder/) based on the human genome "*Homo sapiens* (GRCh38/hg38) -Human (2 Apr. 2014 Updated)" and setting the number of mismatches cutoff ≤4. Potential off-targets have been checked also by CRISPOR (tefor.net/crispor) based on the human genome "*Homo sapiens*-Human-UCSC Dec. 2013 (GRCh38/hg38)".

Selection of sgRNA protospacers was done taking into considerations respective number of potential off-targets and their target position within the DMPK 3'-UTR region. The length of each Sa sgRNA is variable from 21 to 24. Whenever the protospacer did not start with a G, this nucleotide was added to the 5' of the sequence to optimize the U6-driven transcription.

Cell Culture

HeLa cells were cultured in Dulbecco's modified Eagle medium (DMEM) with high glucose and GlutaMAX (Invitrogen), supplemented with 10% Fetal Bovin Serum (FBS, Invitrogen). DM1 cells (iPS-derived MPC) were grown in KnockOut DMEM (Thermo Fisher Scientific) supplemented with 20% FBS, 1% MEM Non-Essential Amino Acids Solution (Thermo Fisher Scientific) and 1% GlutaMAX™ Supplement (Thermo Fisher Scientific). Immortalized WT and DM1 myoblasts were cultivated either in Skeletal Muscle Cell Growth Medium (Promocell) supplemented with 15% FBS, or in DMEM mixed to 199 medium (1:4 ratio; Life Technologies) and supplemented with 20% FBS, 25 µg/ml fetuin, 0.5 ng/ml bFGF, 5 ng/ml EGF and 0.2 µg/ml dexamethasone (Sigma-Aldrich).

Differentiation of myoblasts was induced in confluent cells by replacing the growth medium with differentiation medium (DMEM supplemented with 5 µg/ml insulin).

Standard temperature of 37° C. and 5% $CO_2$ were used to grow and maintain cells in culture.

Transfection Experiments

Cells were seeded the day before transfection in 6 or 12 well plates and transfected at 70-90% of confluency. Transfection reagent FuGENE HD (FuGENE-DNA ratio 3:1; Promega) and lipofectamine 3000 (Thermo Fisher Scientific) were used to transfect HeLa cells and DM1 iPS-derived MPC cells, respectively. Cells were harvested by centrifugation 2-3 days post transfection and cellular pellet was kept at −80° C. until genomic DNA extraction.

Lentiviral Vectors and Transduction Experiments

Lentiviral vectors were produced by transient four-plasmid transfection of 293T cells by calcium phosphate precipitation as previously described (Cantore et al, 2015). Vector titers [vector genome per ml (vg/ml)] were determined by quantitative PCR (qPCR) on genomic DNA of infected HCT116 cells (virus production and titration by Genethon Vector Core and Quality Control Services, respectively).

DM1 myoblasts were seeded the day before transduction in 12 well plates and infected at 70% of confluency. Growth medium was removed before transduction and replaced with minimal volume (400 µl/dish) of transduction medium [skeletal muscle basal medium (Promocell) or DMEM, supplemented with 10% FBS and 4 µg/ml polybrene]. Virus was added directly to the transduction medium and cells were incubated for 5-6 hours before to add full growth medium. At day 1 post-transduction, cells were transferred to 6 well plate and were kept in culture for two passages before to 1) collect and freeze them for gDNA extraction, 2) fix them for FISH/immunofluorescence analysis.

Genomic DNA Extraction and Genomic PCR

Genomic DNA was extracted from HeLa cells and DM1 iPS-derived MPC cells either with GeneJet Genomic DNA purification Kit (Thermo Fisher Scientific) or with QIAmp DNA Micro and Mini Kit (QIAGEN), according to manufacturer's instruction. gDNA extraction from immortalized DM1 myoblasts as well from mice muscles was performed by MagNA Pure 96 system with MagNA Pure LC Total Nucleic Acid Isolation Kit (Roche). Platinum® Taq DNA Polymerase High Fidelity (Invitrogen) was used to amplify DMPK 3'-UTR. PCR master mix was prepared as manufacturer's protocol supplemented with 10% DMSO. PCR was done by using 150 ng of gDNA as template and primers annealing upstream and downstream Cas9 expecting cutting sites (Tab. 2). PCR conditions were the following: 95° C. for 2 min, 35×[95° C. for 30 sec, 52° C. for 30 sec, 72° C. for 30 sec]; 72° C. for 10 min. More cycles (38) and longer extension time (5 min) were used in order to amplify long CTG repeat expansion in DMSXL mice muscles. PCR products were separated by electrophoresis in a 1.5-2% agarose gel containing GelRed DNA stain. Gel images were taken upon UV exposition and adjusted for brightness and contrast.

PCR products were purified by gel extraction (Nucleo-Spin® Gel and PCR Clean-up, Macheray Nageland) and sequenced by Sanger DNA sequencing (Beckman Coulter Genomics).

Fluorescent In Situ Hybridization and Immunofluorescence in DM1 Myoblasts

FISH experiments were done as described by Taneja KL [Taneja K L, 1998] with some modifications [Denis Furling laboratory, Institut de Miologie, Paris]. Briefly, cells cultivated in chamber slides (Corning) were washed in phosphate-buffered saline (PBS) and fixed in 4% paraformaldehyde (PFA). After fixation, cells were washed in PBS and stored in 70% ethanol at 4° C. Cells were hydrated in PBS and incubated with probe Cy3-labeled 2'OMe (CAG)7 (Sigma-Aldrich) in hybridization buffer (40% formamide, 2× saline-sodium-citrate (SSC), 0.2% BSA). After hybridization, microscopy slides were washed several times before to permeabilize cell membrane in PBS/0.25% TritonX-100. SaCas9 was detected by antibodies directed against the HA tag epitope located at the C-terminus of the protein. Purified mouse monoclonal anti-HA tag (Covance) was used as primary antibody at dilution 1/400 in 5% BSA and incubated for 1 h 30 min at RT. Goat anti-mouse 633 secondary antibody (Themo Fisher Scientific) was used at dilution 1/1000 in 5% BSA and incubated for 1 h at RT. Mounting solution with DAPI (Southern Biotech) was used to assemble microscopy slides with cover slips. Microscopy images were acquired with a confocal microscope (Leica DMi8), analyzed with Leica Application Suite X software, and processed either with Adobe Photoshop or with ImageJ software.

Southern Blot Analysis

Genomic DNA was extracted from WT and DM1 immortalized cell lines as described above. Approximately 5 µg of gDNA was digested with EcoRI restriction enzyme at 37° overnight. Digested DNA was resolved on a 0.7% agarose gel for ~16 h at 50V. After migration, agarose gel was incubated for 1 h in 1M NaOH solution, to denaturate the DNA, and then for 2 h in Neutralization buffer (1M Tris, 3M NaCl pH 8.5). Genomic DNA fragments were transferred from the gel to Genescreen Plus Hybridization membrane (Perkin Elmer) via capillary action in 6× SSC buffer, and crosslinked to membrane using the Stratalinker UV crosslinker. DNA was hybridized with $2*10^6$ cpm/mL of 1.4 kb BamHI probe (B1.4) covering the region of DMPK CTG repeat (Gourdon et al, 1997). Probe was pre-labeled with High Prime DNA labeling Kit (Sigma) and hybridization was performed at 68° C. overnight in PerfectHyb Plus Hybridization buffer (Sigma) containing 50 µg/mL Human Cot-1 DNA (Thermo Fisher Scientific). Signal was revealed by using Phosphorimager.

RT-PCR for Alternative Splicing

Total RNA was isolated using TRIzol reagent (Life Technologies) according to the manufacturer's protocol. RT-PCR was done as described by Arandel and colleagues (Arandel et al, 2017). Briefly one µg of RNA was reverse transcribed by M-MLV reverse transcriptase (Life Technologies) and one µl of cDNA preparation was used for the PCR (Reddy-Mix, Thermo Fisher Scientific) with primers listed in Table 2. PCR products were separated by 2% agarose gel electrophoresis and visualized with GelRed DNA stain upon UV exposition. Optical density of each PCR band was quantified using ImageJ software and percentage of exon inclusion was calculated as [exon inclusion band/(summa exon inclusion+exclusion bands)]*100.

Animals and AAV Vectors Injections

DMSXL mice (90% C57BL/6 background) carrying 45 kb of human genomic DNA cloned from a DM1 patient were used for the in vivo study [Huguet et al, 2012]. Transgenic status was assayed by PCR as described by Gomes-Pereira and collaborators [Gomes-Pereira et al, 2007]. Housing and handling of mice were performed in accordance with the guidelines established by the French Council on animal care "Guide for the Care and Use of Laboratory Animals": EEC86/609 Council Directive—Decree 2001-131.

rAAV vectors were produced and titrated by Genethon Vector Core and Quality Control Services, as previously described (Ronzitti et al, 2016).

Intramuscular injections were done into DMSXL mice at three and six weeks of age anesthetized by ketamine/xylazine mixture. AAV virus was injected into the left TA ($0.6*10^{\wedge 11}$ and $1*10^{\wedge 11}$ total Vg/TA at three and six weeks, respectively); PBS was injected into the right TA, as control. Four weeks post-injection, TAs muscles were collected and frozen in liquid nitrogen.

RESULTS

Sa Cas9 and sgRNA Expression Cassettes

The Cas9 investigated in the study is Cas9 from *S. aureus* (SaCas9). This endonuclease is of particular interest because SaCas9 is of small size and can fit into an adeno-associated virus (AAV) vector. All the plasmids containing Sa Cas9 and the Sa sgRNA scaffold derived from plasmid pX601-AAV-CMV::NLS-SaCas9-NLS-3xHA-bGHpA; U6::BsaI-sgRNA (Feng Zhang Lab, Addgene number #61591, FIG. 1). In order to include in the same vector Sa Cas9 and two sgRNA cassettes, the original CMV promoter was first replaced with the smaller EFS (FIG. 1, MLS43). Expression of Sa Cas9 and its nuclear localization were verified by western blotting and immunofluorescence with Abs directed against the HA epitope (data not shown). Next, a second cassette was added for the sgRNA, identical to that one already existing, but with a different cloning site for the sgRNA protospacer (FIG. 1, MLS47).

Sequence of sgRNAs proto spacer (corresponding to guide sequence of sgRNA) are listed in FIG. 2, they target a genomic region upstream or downstream the CTG repeat that goes from the stop codon of the gene DMPK to the polyA signal. Position of all sgRNAs tested within the DMPK 3'-UTR are indicated in FIG. 3.

sgRNAs were tested for their capability to cut the DNA at their genomic target. Briefly, HeLa cells were transfected with plasmids harboring Sa Cas9 and only one sgRNA (protospacer cloned in BbsI site) and collected 2-3 days post transfection. Genomic DNA extracted from those transfected cells was used as template to PCR amplify DMPK 3'-UTR region surrounding the genomic targets of each sgRNA. PCR products were sent for sequencing and the chromatogram file of transfected and untransfected cells were used to analyse the cutting efficiency by the on line program TIDE (tide-calculator. nki.nl/).

Results of TIDE analysis are shown in the last column of the table of FIG. 2.

This last column of the table shows that the cutting efficiency varies among the sgRNA protospacers tested. In particular, all upstream protospacers tested (1, 4, 7, 8B) were very efficient, having a cutting percentage by TIDE comprised between 42 and 47.4%. Concerning downstream protospacers, the inventors have surprisingly found that some of them are more efficient for cutting region downstream the CTG repeat. In particular, six downstream protospacers (10, 15B, 22, 17A, 17B and 19) have weak cutting percentage, ranging from 1.1 to 7.9%, whereas the downstream proto spacer 23 was particularly efficient for cutting DNA, with cutting percentage of 48.3%.

Those results show that all sgRNAs do not behave at all with the same efficiency in terms of DNA cutting and that, unexpectedly, downstream sgRNA 23 is particularly effective to cut DNA downstream the CTG repeat expansion.

Sa Cas9-Mediated Deletion of the CTG Repeat in the Human DMPK Gene

We then tested the efficacy of the CRISPR-Cas9 system using SaCas9 combined with appropriate sgRNAs in the human DMPK locus in the presence of a pathological CTG expansion. In order to delete the CTG repeat expansion, we made constructs harboring in the same plasmid Sa Cas9 and two sgRNAs, one targeting the region upstream the CTG repeat and the other targeting the region downstream the CTG repeat (cloned in BbsI and BsaI sites of plasmid MLS47, respectively, see FIG. 1).

The sgRNAs couples were selected based on their single cut efficiency (TIDE analysis, FIG. 2). More precisely, upstream sgRNA 1, 4, 7 and 8B were each tested with downstream sgRNA 23 which presented the highest cutting percentage as compared to downstream sgRNAs 10, 15B, 17A, 17B, 19 and 22.

Plasmids harboring Sa Cas9 and the indicated sgRNA couples were used to transfect HeLa cells or DM1 cells (iPS-derived MPC from I-Stem, Evry). DMPK 3'-UTR was PCR amplified as described in material and methods and PCR products were separated into 1.5% agarose gel (FIG. 4). Bands relative to full length products and to products containing the CTG repeat deletion were extracted from the agarose gel and verified by sequencing. Annealing between the undeleted wild type DMPK 3'-UTR region and the deleted one is showed in FIG. 5 and highlight the cutting site for each sgRNA couples tested (i.e. between nucleotide $N_3$ and $N_4$ of the proto spacer).

Altogether, these results show that the described SaCas9-sgRNA system is suitable for efficiently excising the CTG repeat from the 3'-UTR region of the human DMPK gene.

It also shows that the selection of the downstream sgRNA is an important parameter to obtain efficient excision of a CTG repeat from the 3'-UTR region of the DMPK gene.

In summary, the present inventors identified specific sgRNA protospacers that lead to efficient single cutting efficiency when used with Cas9 endonuclease derived from *S. aureus*. Moreover, they proved that CRISPR-Cas9 system using SaCas9 endonuclease in combination with appropriate sgRNAs was suitable and efficient for excising the CTG repeat from the DMPK 3'UTR.

CRISPR-Cas9-Mediated Deletion of Long CTG Repeat Expansion in DM1 Patient Cell Lines.

In order to test the ability of CRISPR-Cas9 in deleting a long CTG repeat expansion, we employed immortalized DM1 cells from patient harboring 2600 CTG repeats (Arandel et al, 2017). We constructed lentiviral vectors for SaCas9 and sgRNAs, as these viruses are known to transduce myoblasts with high efficiency. Representation of the lentiviral constructs is depicted in FIG. 6A: SaCas9 is under the control of the CMV promoter, the couple of two sgRNAs, targeting the region upstream and downstream the CTG repeat (UP and DW), are in tandem and both under the control of the U6 promoter. A GFP expression cassette was also included into the sgRNA lentiviral vector in order to follow the sgRNA expression within the cells.

DM1 cells have been transduced with increasing MOI (Multiplicity Of Infection) of Cas9 and sgRNAs lentiviral vectors and tested for the CTG deletion by genomic PCR (FIG. 6B). PCR was performed as described in section Materials and Methods and using couple of primers F1-DMPK-3UTR and R1-DMPK-3UTR. gDNA from untreated cells (−/−) or cells transduced only with 50 MOI of sgRNA lentiviral vector (−/50) were used as negative controls. The band at lower molecular weight (303 bp for couple 4-23, and 414 bp for couple 8B-23) represents the PCR product with genomic deletion of the CTG repeats, without discrimination between expanded and unexpanded alleles. Band at higher molecular weight represents the PCR product of the undeleted genomic region with unexpanded CTG repeat (870 bp). We were not able to PCR amplify the expanded undeleted CTG repeat because the magnitude of the length (2600 repeats correspond to a PCR product longer than 8600 bp). Our results showed that there is a correlation between amount of viral particles inoculated and the intensity of the PCR bands: at increasing MOI of vectors we could observe increasing intensity of the band relative to the CTG deletion and decreasing intensity of the band relative to undeleted PCR products. These data showed that Cas9 and selected sgRNAs couples 4-23 and 8B-23 can lead to an efficient deletion of the CTG repeat in vitro.

Next, we were interested in understanding if the CTG deletion influences the presence of the nuclear foci. Thus, we selected the DM1 cells transduced with both vectors at high MOI (25 and 50) and we performed FISH analysis. DM1 cells untreated or treated only with one of the two vectors were used as controls. After image acquisition by confocal microscopy, we manually counted the number of cells where foci disappeared, and reported this number as percentage of the entire population (FIG. 6C). To be noticed, not all the cells have been infected by both lentiviral vectors, thus the percentage reported in FIG. 6C would be higher if normalized for double positive cells Cas9-sgRNAs. As observed for the PCR deletion, also the disappearance of foci correlates with the amount of viral particles inoculated, and number of cells without foci was higher at the at highest MOI used in this study (MOI 50).

Our data showed that CRISPR-Cas9-mediated CTG repeat excision determines the disappearance of foci into the nuclei.

Results obtained by genomic PCR showed that Cas9 and selected sgRNAs can delete the CTG repeat at the 3'-UTR of the DMPK gene but did not distinguish between deletion of allele with non-pathological number of CTG repeat (n equal to 13) and that with expanded CTG repeat (n equal to 2600). In order to do so, we isolated DM1 single clones after treatment with CRISPR-Cas9 lentiviral vectors, and performed southern blot analysis of EcoRI-digested genomic DNA. Relative position of EcoRI restriction sites within the DMPK, as well the expected cutting site for Cas9, and region recognized by the radioactive probe used for the southern hybridization are represented in FIG. 7A. In particular, we selected a DM1 Delta clone showing 1) 100% deletion of the CTG repeat by PCR and 2) absence of nuclear foci. DM1 clones Ctrl 1 (negative for Cas9 and sgRNA) and Ctrl 2 (negative for Cas9 but positive for sgRNA) were used as controls. We also used as non-pathological control, immortalized wild type myoblast (WT) harboring 5 and 14 CTG repeats. Southern blot analysis showed that DM1 Delta clone has a CTG repeat deletion in both alleles, with and without expansion (FIG. 7B). Discrimination of the two alleles was possible because the presence of an Alu polymorphism between the two EcoRI restriction sites. This means that upon EcoRI genomic DNA digestion, we will obtain two bands ~1 kb different in size, one for the allele with Alu polymorphism (corresponding to the allele with CTG expansion in DM1 cells) and one for the allele without Alu (corresponding to allele without CTG expansion in DM1 cells, i.e. the allele with non-pathological number of CTG). Same Alu polymorphism is also present in wild type myoblasts. List of CTG repeat number [(CTG)n] per allele, and expected size of the EcoRI bands is reported in FIG. 7C.

These results demonstrates that Cas9 and selected sgRNAs can delete the CTG repeat at the 3'-UTR of both alleles of the DMPK gene, i.e. the allele with non-pathological number of CTG repeat and the allele with expanded CTG repeat (equal to 2600).

Splicing Profile Analysis in DM1 Cells After Genomic Excision of the CTG Repeat Expansion.

Same cells and DM1 clones analyzed for the CTG excision by southern blot (FIG. 7) have been used to analyze the alternative splicing profile of several transcripts known to be deregulated in skeletal muscle of DM1 patients, as well in immortalized DM1 myoblast from patient (Arandel et al, 2017). Cells have been differentiated in myotubes (see Material and Methods) and then collected for RNA extraction. Primers specific for the transcripts analyzed are listed in Tab 2. Results of the RT-PCR are shown in FIG. 8: for each transcript, a representative image of the RT-PCR gel is reported on the left (FIG. 8A) and quantification of exon inclusion is represented on the right (FIG. 8B). All the six transcripts analyzed showed correction of the splicing anomalies in the DM1 Delta clone. In particular transcripts LDB3, SERCA1, MBNL1 and DMD showed a reversion that reached the same level of the wild type (WT). IR and BIN1 reversion was less pronounced but still statistically different from the DM1 control clones Ctrl 1 and 2. Overall, these results show that excision of the CTG repeat expansion in DM1 cells reverts the DM1 splicopathy.

AAVs Cas9 and sgRNA Induce Deletion of the CTG Repeat Expansion In Vivo in DMSXL Mice.

In order to verify the ability of our sgRNA couples to induce CTG repeat deletion in vivo, we choose DMSXL mice as animal model for the DM1 disease (Huguet et al, 2012). DMSXL mice harbor one copy of the human DMPK gene with ~1200 CTG repeats, and reproduce many features of the human pathology, as presence of nuclear foci, splicing defects, and muscle weakness. In order to deliver the CRISPR-Cas9 system into the muscle tissue of DMSXL mice, we constructed Adeno-Associated Virus (AAV) vectors for SaCas9 and sgRNAs. AAVs are known to efficiently infect muscles but they have a limited packaging capacity of ~4.7 Kb (Warrington et al, 2006; Buj-Bello et al, 2008). For this reason, we designed two AAVs, one for Cas9 and the other for the two sgRNAs in tandem. SaCas9 is under the control of SPc5-12, a small synthetic promoter that drives a good expression of the transgene in muscle (Li et al, 1999). Sequence related to sgRNAs couple 4-23 and their U6 promoters was PCR amplified from the corresponding lentiviral construct shown in FIG. 6 and cloned in an AAV plasmid downstream the polyadenylation sequence of a Desmin promoter driven eGFP-K expression cassette, where K is the Kash peptide for nuclear membrane localization (FIG. 9A).

Both AAVs for Cas9 and sgRNA 4-23 have been co-injected in the left tibialis anterior (TA) of heterozygous DMSXL mice at three and six weeks of age ($0.6*10^{11}$ and $1*10^{11}$ total Vg). Four weeks later, mice have been euthanized and muscles collected. In order to detect the CTG repeat deletion, PCR was performed with genomic DNA extracted from TA and primers F1-DMPK-3UTR and R2-DMPK-3UTR (see Materials and Methods). gDNA from right TA, injected only with PBS, was used as negative control (−). Results of the genomic PCR are presented in FIG. 9B. All TA that have been injected with AAVs Cas9-sgRNA (+) showed a PCR band corresponding to the expected size for the amplicon with a CTG repeat deletion (399 bp). The PCR product relative to undeleted CTG repeat expansion is hardly amplified because the length of the repeats and is shown in FIG. 9C (expected size 4527 bp). Our results demonstrated that Cas9, in association with couple sgRNAs 4-23, is able to in vivo delete a long CTG repeat expansion at the 3'-UTR of the human DMPK gene in the DMSXL mice model.

The invention claimed is:

1. A pair of sgRNA molecules, wherein:
said pair comprises first and second sgRNA molecules that are able to bind by base-pairing to target sequences within a DMPK gene, the DMPK gene comprising a nucleotide repeat expansion located within a 3'-untranslated region (3'-UTR) of the gene,
wherein said first sgRNA molecule is able to bind to, and induce a double strand break within said 3' UTR at a position 5' of said nucleotide repeat expansion in the presence of a Cas9 endonuclease;
wherein said second sgRNA molecule is able to bind to, and induce a double strand break within, said 3'-UTR at a position 3' of said nucleotide repeat expansion in the presence of a Cas9 endonuclease;
wherein said Cas9 endonuclease is derived from *Staphylococcus aureus* (SaCas9), or wherein said Cas9 endonuclease is a functional variant of a SaCas9; and
wherein said second sgRNA molecule comprises a guide sequence of 20-30 nucleotides comprising the nucleotide sequence shown in SEQ ID NO:11.

2. The sgRNA pair of claim 1, wherein the first sgRNA comprises a guide sequence of 20-30 nucleotides in length comprising the nucleotide sequence shown in SEQ ID NO:7, SEQ ID NO:8, SEQ ID NO:9 or SEQ ID NO:10.

3. The sgRNA pair of claim 1, wherein the guide sequence of the first sgRNA consists of a nucleotide sequence selected from SEQ ID NOs:1-4 and SEQ ID NO:18.

4. The sgRNA pair of claim 1, wherein the guide sequence of the second sgRNA consists of a nucleotide sequence as shown in SEQ ID NO:5.

5. A sgRNA comprising a sequence that is able to bind by base-pairing to a target genomic DNA sequence located within a DMPK gene, the DMPK gene comprising a nucleotide repeat expansion within a 3' UTR of the DMPK gene;
wherein the sgRNA molecule is able to bind to, and induce a double strand break within, said 3'-UTR at a position either 5' or 3' of said nucleotide repeat expansion in the presence of a Cas9 endonuclease derived from *Staphylococcus aureus* (SaCas9) or a Cas9 endonuclease that is a functional variant of a SaCas9, and
wherein said sgRNA comprises a guide sequence of 20-30 nucleotides comprising a sequence selected from the group consisting of SEQ ID NO:8 and SEQ ID NO:11.

6. The sgRNA of claim 5, wherein said sgRNA comprises a guide sequence selected from the group consisting of SEQ ID NO:2, SEQ ID NO:5 and SEQ ID NO:18.

7. A vector encoding a sgRNA of claim 5.

8. The vector of claim 7, wherein said vector is a plasmid, a viral vector, a rAAV vector or a lentiviral vector.

9. A target cell transfected or transduced with the vector according to claim 7.

10. A method for the production of a sgRNA comprising culturing the target cell according to claim 9 in conditions allowing production of said sgRNA and recovering said sgRNA produced in said culturing step.

11. An in vitro method for excising a nucleotide repeat located within a non-coding region of a DMPK gene in a cell, comprising introducing into said cell a pair of sgRNA molecules according to claim 1, or a vector encoding said pair of sgRNA molecules, and a Cas9 endonuclease derived from *S. aureus*.

12. A method of treating myotonic dystrophy type 1 comprising administering a sgRNA pair according to claim 1 and a Cas9 endonuclease derived from *S. aureus* to a subject having myotonic dystrophy type 1.

13. The method of claim 12, wherein the nucleotide repeat expansion is a trinucleotide repeat expansion located within the 3'-UTR of the DMPK gene.

14. The method according to of claim 13, wherein the nucleotide repeat expansion comprises 20 or more repeats.

15. A pharmaceutical composition comprising:
a) the pair of sgRNA molecules according to claim 1;
b) a vector encoding said pair of sgRNA; or
c) a cell comprising said vector.

16. A pharmaceutical composition comprising:
a) the pair of sgRNA molecules according to claim 5;
b) a vector encoding said pair of sgRNA; or
c) a cell comprising said vector.

17. A vector encoding the pair of sgRNA molecules according to claim 1.

18. The vector of claim 17, wherein said vector is a plasmid, a viral vector, a rAAV vector or a lentiviral vector.

19. A target cell transfected or transduced with the vector according to claim claim 17.

20. A method for the production of a pair of sgRNA molecules comprising culturing the target cell according to claim 19 in conditions allowing production of said pair of sgRNA molecules, and recovering said pair of sgRNA molecules produced in said culturing step.

21. The method of claim 14, wherein the nucleotide repeat expansion comprises from 20 to 10000 repeats.

22. The method of claim 14, wherein the nucleotide repeat expansion comprises from 50 to 5000 repeats.

* * * * *

UNITED STATES PATENT AND TRADEMARK OFFICE
CERTIFICATE OF CORRECTION

PATENT NO. : 11,427,824 B2
APPLICATION NO. : 16/345743
DATED : August 30, 2022
INVENTOR(S) : Ana Maria Buj Bello and Mirella Lo Scrudato It is certified that error appears in the above-identified patent and that said Letters Patent is hereby corrected as shown below:

In the Specification

Column 3,
Line 35, "proto spacer." should read --protospacer.--.

Column 5,
Line 15, "region (A" should read --region (Δ--.
Line 18, "proto spacer)." should read --protospacer).--.
Line 36, "agaro se gel" should read --agarose gel--.

Column 8,
Line 53, "proto spacer)" should read --protospacer)--.

Column 10,
Line 39, "GCA" should read --G̲CA--.

Column 16,
Line 32, "Sal/I/AgeI" should read --*Sal*I/*Age*I--.

Column 25,
Line 62, "proto spacer" should read --protospacer--.

Column 26,
Line 29, "proto spacer)." should read --protospacer).--.

Signed and Sealed this
Fifteenth Day of August, 2023

Katherine Kelly Vidal
*Director of the United States Patent and Trademark Office*